United States Patent
Rosenbluth et al.

(10) Patent No.: US 6,511,492 B1
(45) Date of Patent: Jan. 28, 2003

(54) EMBOLECTOMY CATHETERS AND METHODS FOR TREATING STROKE AND OTHER SMALL VESSEL THROMBOEMBOLIC DISORDERS

(75) Inventors: Robert F. Rosenbluth, Laguna Niguel, CA (US); Brian J. Cox, Laguna Niguel, CA (US); George R. Greene, Jr., Costa Mesa, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

(21) Appl. No.: 09/071,561

(22) Filed: May 1, 1998

(51) Int. Cl.[7] .............................................. A61B 17/22

(52) U.S. Cl. ...................... 606/159; 606/200

(58) Field of Search ................. 606/1, 110, 113, 606/127, 159, 167, 200

(56) References Cited

U.S. PATENT DOCUMENTS

| | | |
|---|---|---|
| 3,635,223 A | 1/1972 | Klieman |
| 3,923,065 A | 12/1975 | Nozick et al. |
| 3,996,938 A | 12/1976 | Clark |
| 4,030,503 A | 6/1977 | Clark, III |
| 4,046,150 A | 9/1977 | Schwartz et al. |
| 4,347,846 A | 9/1982 | Dormia |
| 4,425,908 A | 1/1984 | Simon |
| 4,590,938 A | 5/1986 | Segura et al. |
| 4,643,184 A | 2/1987 | Mobin-Uddin |
| 4,706,671 A | 11/1987 | Weinrib |
| 4,790,812 A | 12/1988 | Hawkins |
| 4,807,626 A | 2/1989 | McGirr |
| 4,873,978 A | 10/1989 | Ginsburg |
| 5,011,488 A | 4/1991 | Ginsburg |
| 5,034,001 A * | 7/1991 | Garrison et al. ............ 606/198 |
| 5,057,114 A | 10/1991 | Wittich et al. |
| 5,059,178 A | 10/1991 | Ya |
| 5,092,839 A | 3/1992 | Kipperman |
| 5,464,408 A * | 11/1995 | Duc ............................ 606/108 |
| 5,527,326 A | 6/1996 | Hermann et al. |
| 5,649,953 A * | 7/1997 | Lefebvre ..................... 606/200 |
| 5,814,064 A * | 9/1998 | Daniel et al. ................ 606/159 |
| 5,895,398 A | 4/1999 | Wensel et al. |
| 5,895,411 A | 4/1999 | Irie |
| 5,908,435 A * | 6/1999 | Samuels ...................... 606/200 |
| 5,941,896 A * | 8/1999 | Kerr ............................ 606/200 |

FOREIGN PATENT DOCUMENTS

| | | |
|---|---|---|
| WO | WO9920189 | 4/1999 |
| WO | WO9923952 | 5/1999 |

OTHER PUBLICATIONS

Baxter Healthcare Corporation, Vascular Systems Division, A Fogarty Catheter with a new twist.

(List continued on next page.)

*Primary Examiner*—Glenn K. Dawson
(74) *Attorney, Agent, or Firm*—Robert D. Buyan; Stout, Uxa, Buyan & Mullins, LLP

(57) ABSTRACT

Embolectomy catheters, rapid exchange microcatheters, systems and methods for removing obstructive matter (e.g., thrombus, thromboemboli, embolic fragments of atherschlerotic plaque, foreign objects, etc.) from blood vessels. This invention is particularly useable for percutaneous removal of thromboemboli or other obstructive matter from small blood vessels of the brain, during an evolving stroke or period of cerebral ischemia. In some embodiments, the embolectomy catheters of this invention are advanceable over a guidewire which has been pre-inserted through or around the obstructive matter. Also, in some embodiments, the embolectomy catheters include obstructive matter capturing receptacles which are deployable from the catheter after the catheter has been advanced at least partially through the obstructive matter. Such obstructive matter capturing receptacles may include i) at least one proximal strut which are designed to be retractable through a blood clot and ii) a distal matter-receiving portion which is designed to prevent a blood clot from passing therethrough.

23 Claims, 13 Drawing Sheets

OTHER PUBLICATIONS

Broderick JP, Dept. of Neurology, University of Cincinnati Medical Center, Ohio, USA, Recanalization therapie for actue ischemic stroke, Aug. 4, 1999, http://www.ncbi.nlm.nih.gov/htbin–p . . . uery?uid=9932618 . . .

Hill B, Fogarty TJ, Department of Surgery, Stanford University School of Medicine, CA, USA, The use of the Fogarty catheter in 1998, Aug. 4, 1999, http://www.ncbi.nlm.nih.gov/htbin–p . . . ery?uid=10386742 . . .

Parsons Re et al., Department of Surgery, Montefiore Medical Center, University Hospital, Albert Einstein College of Medicine, New York, NY, USA, Fluoroscopically assisted thromboembolectomy: an improvd method for treating acute arterial occlusions, Aug. 4, 1999, http://www.ncbi.nlm.nih.govhtbin–p . . . uery?uid=8792986 . . . .

* cited by examiner

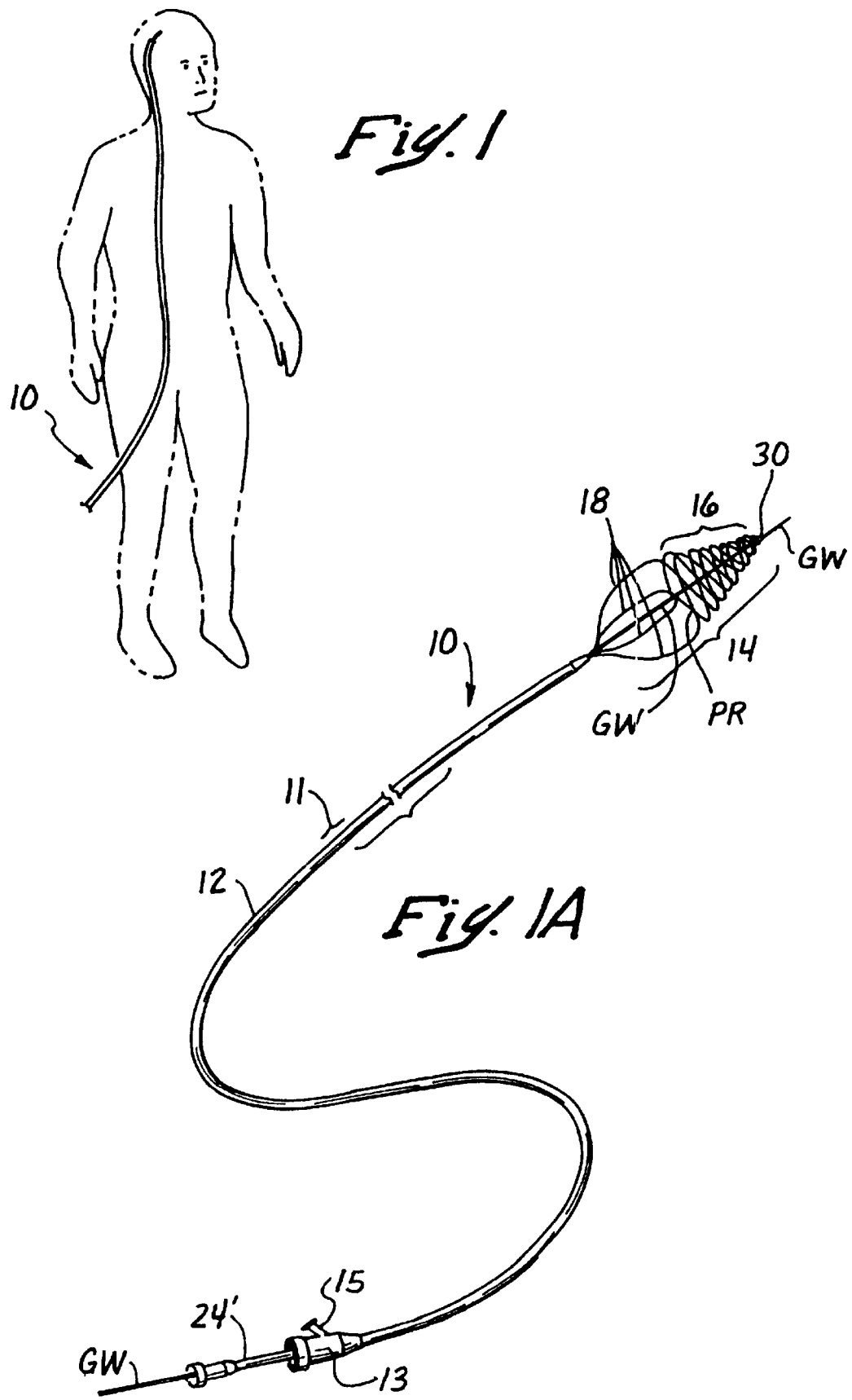

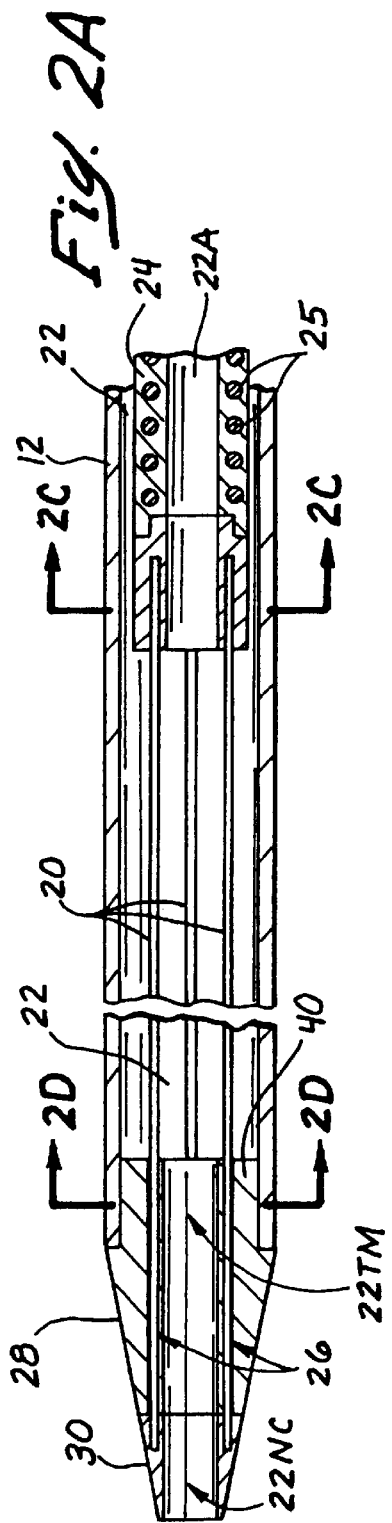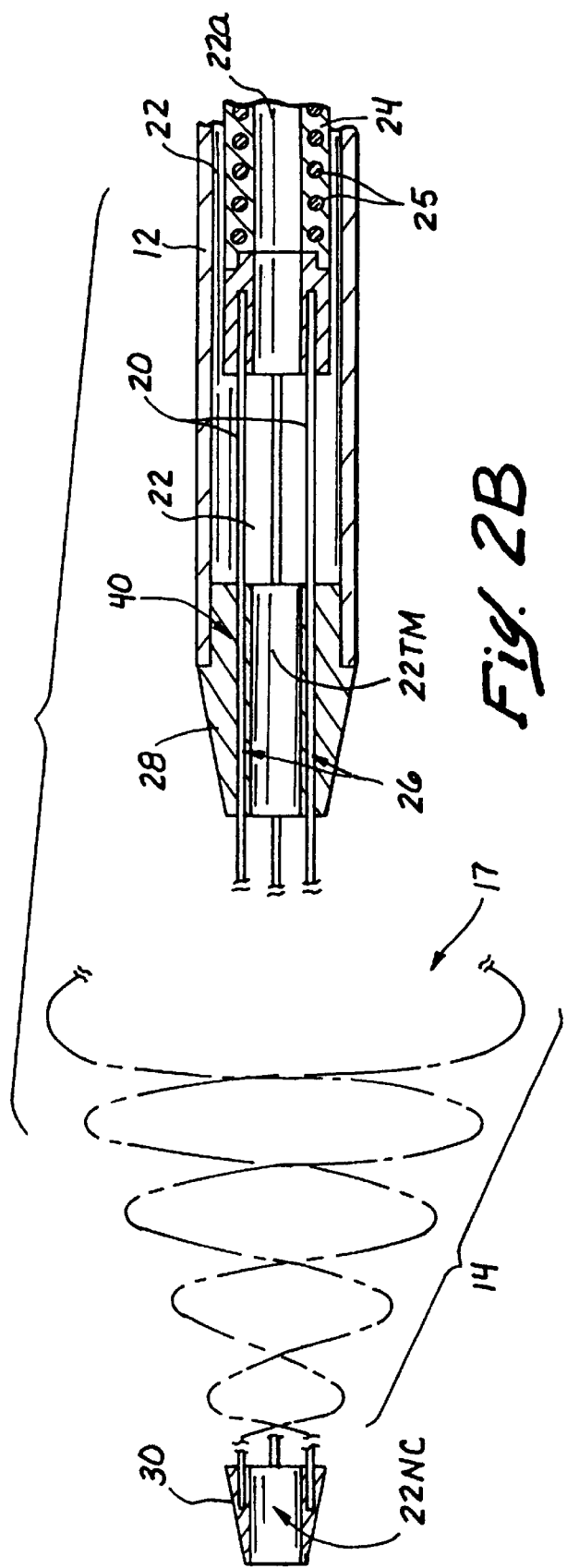

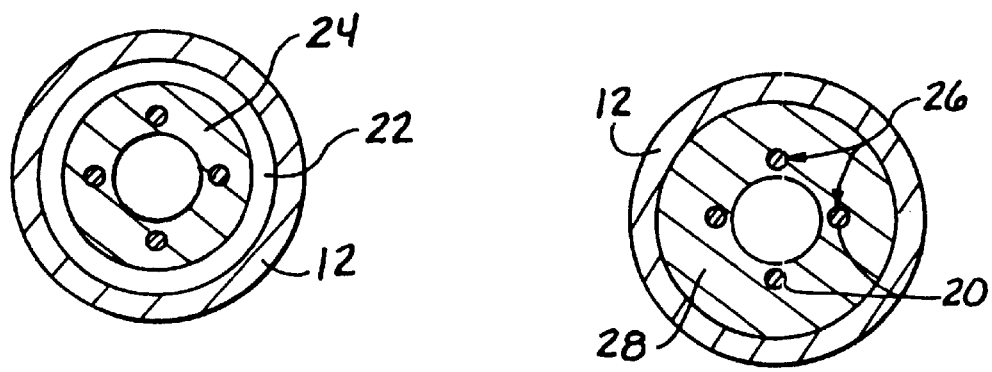
Fig. 2C
Fig. 2D
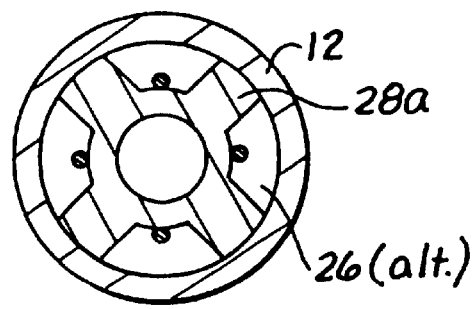
Fig. 2D'
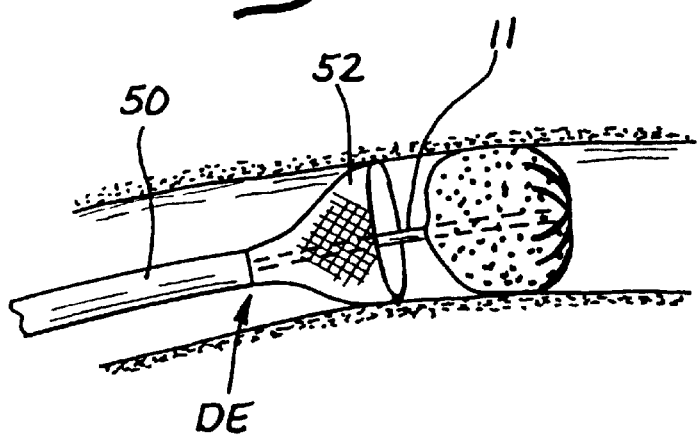
Fig. 6

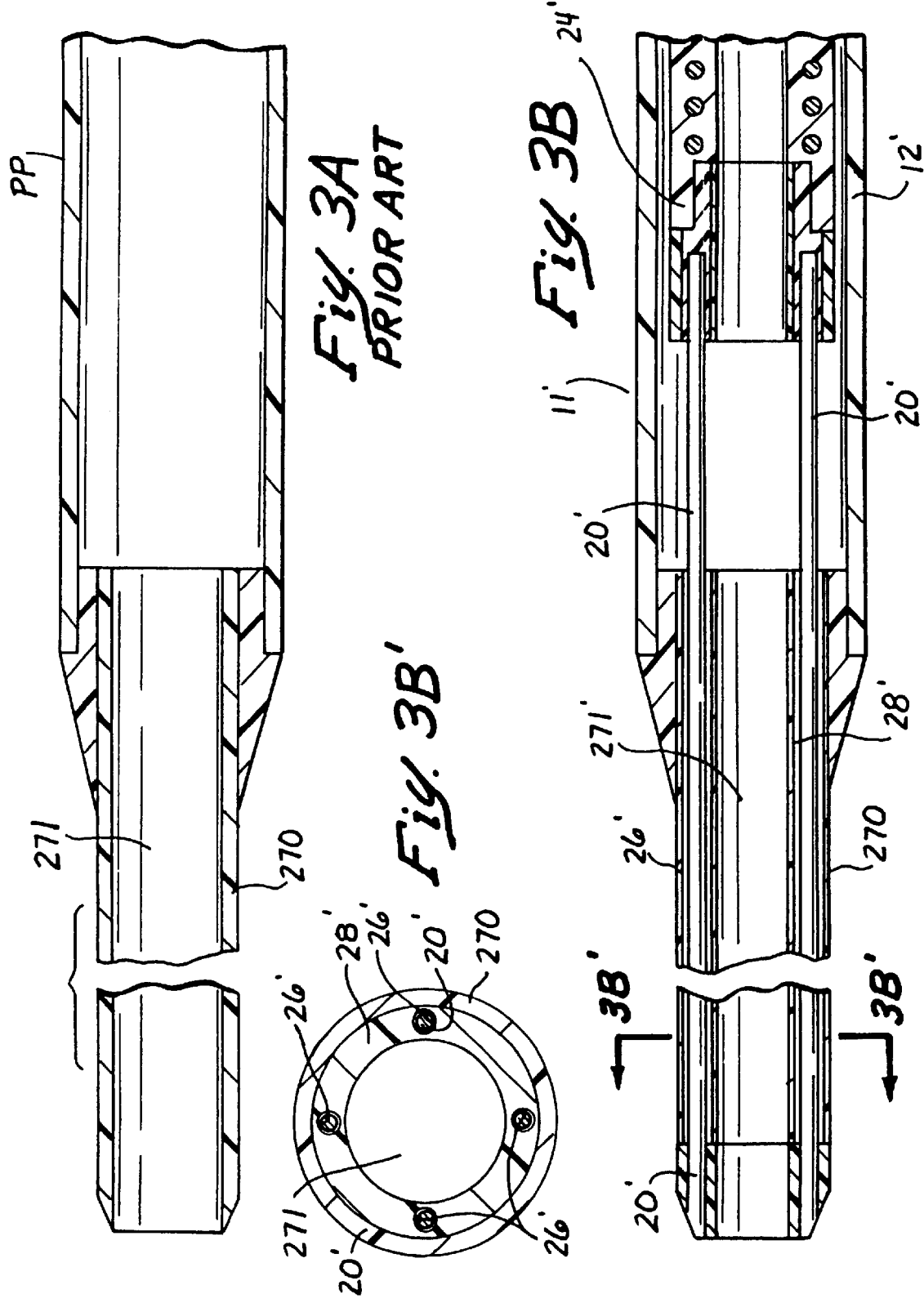

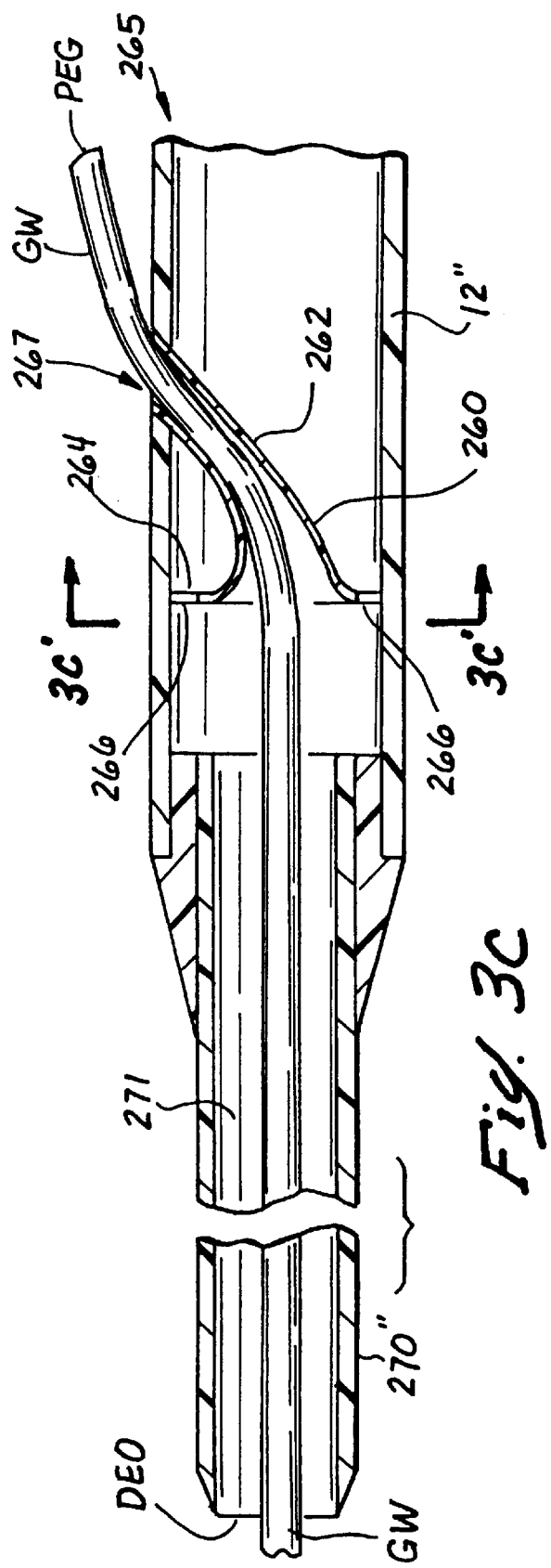
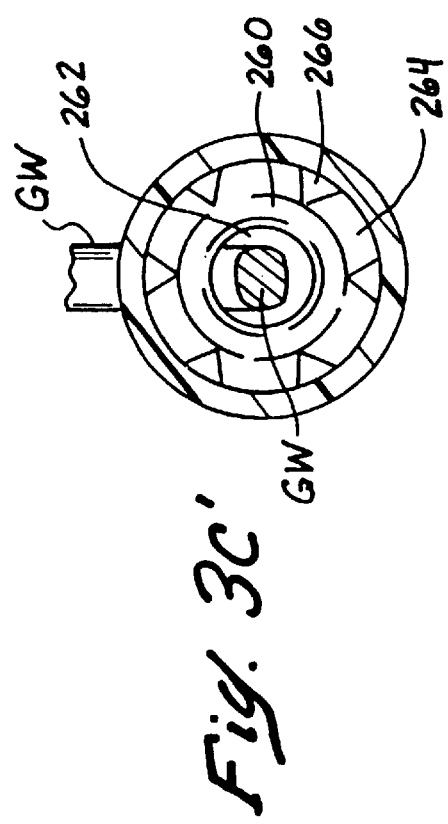
Fig. 3C
Fig. 3C'

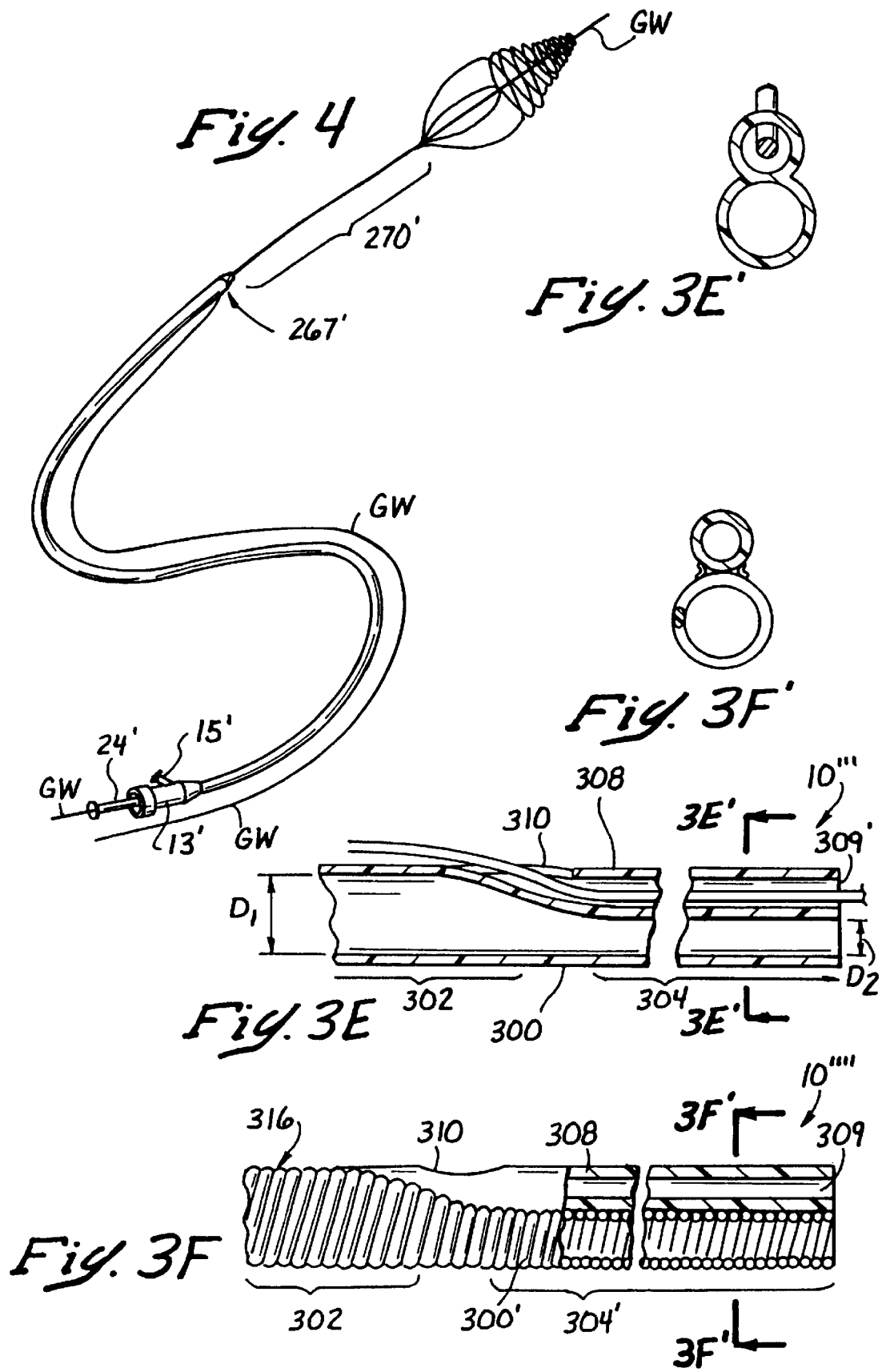

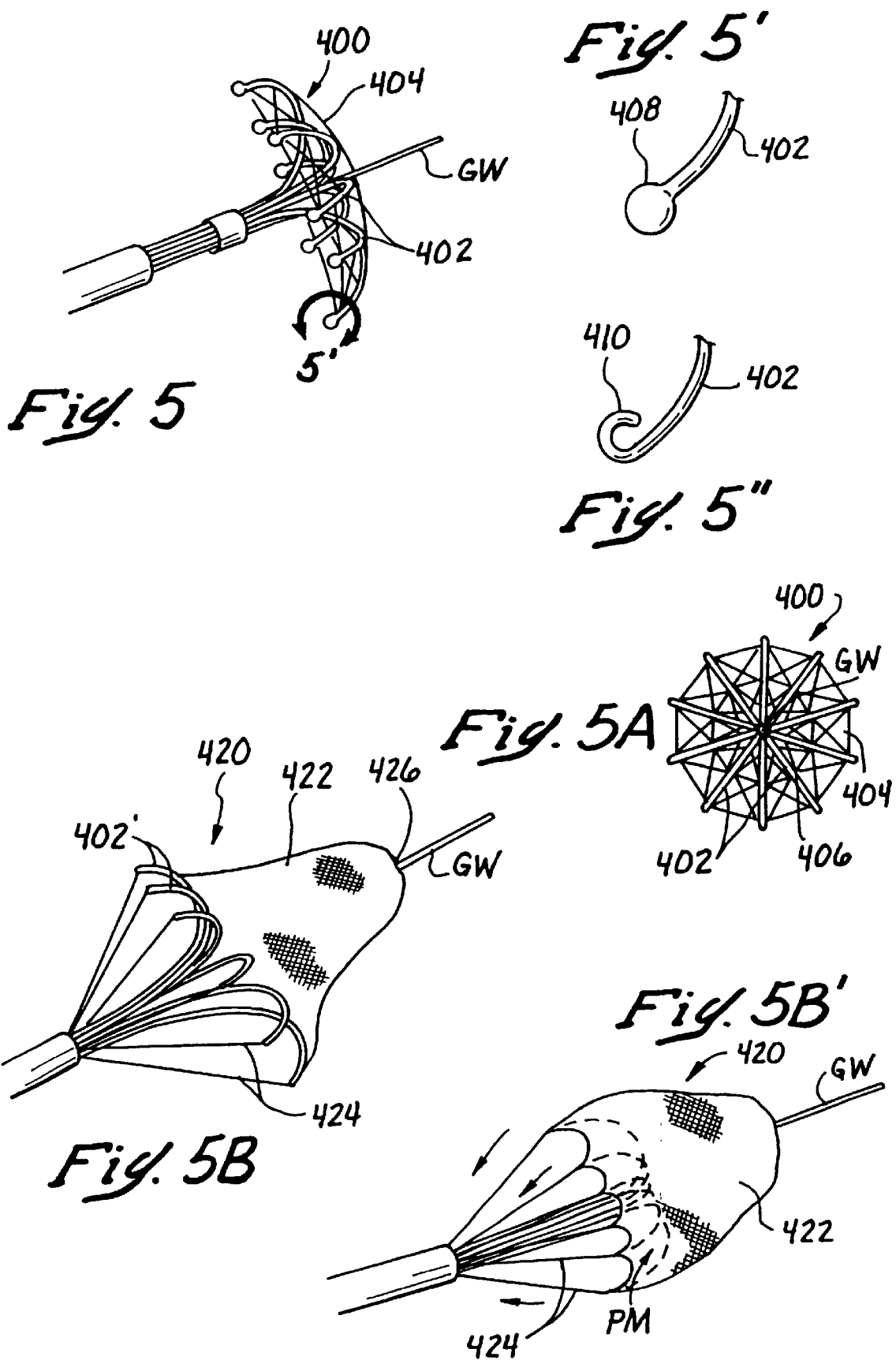

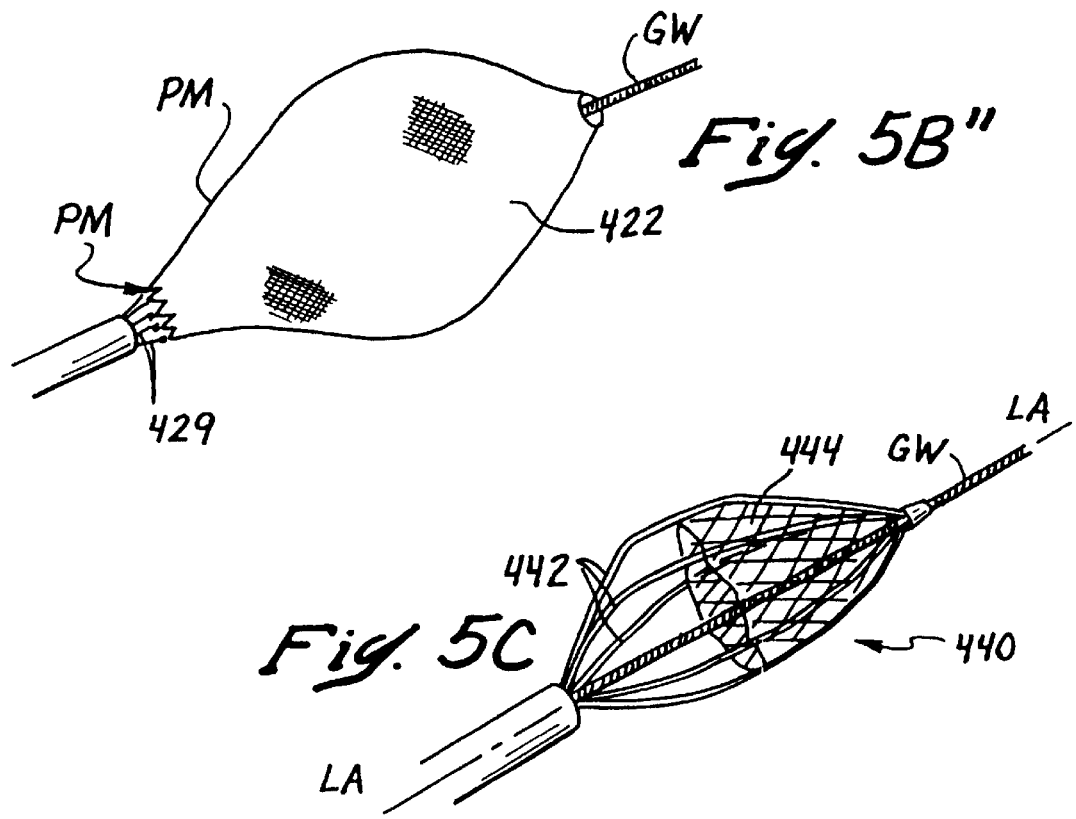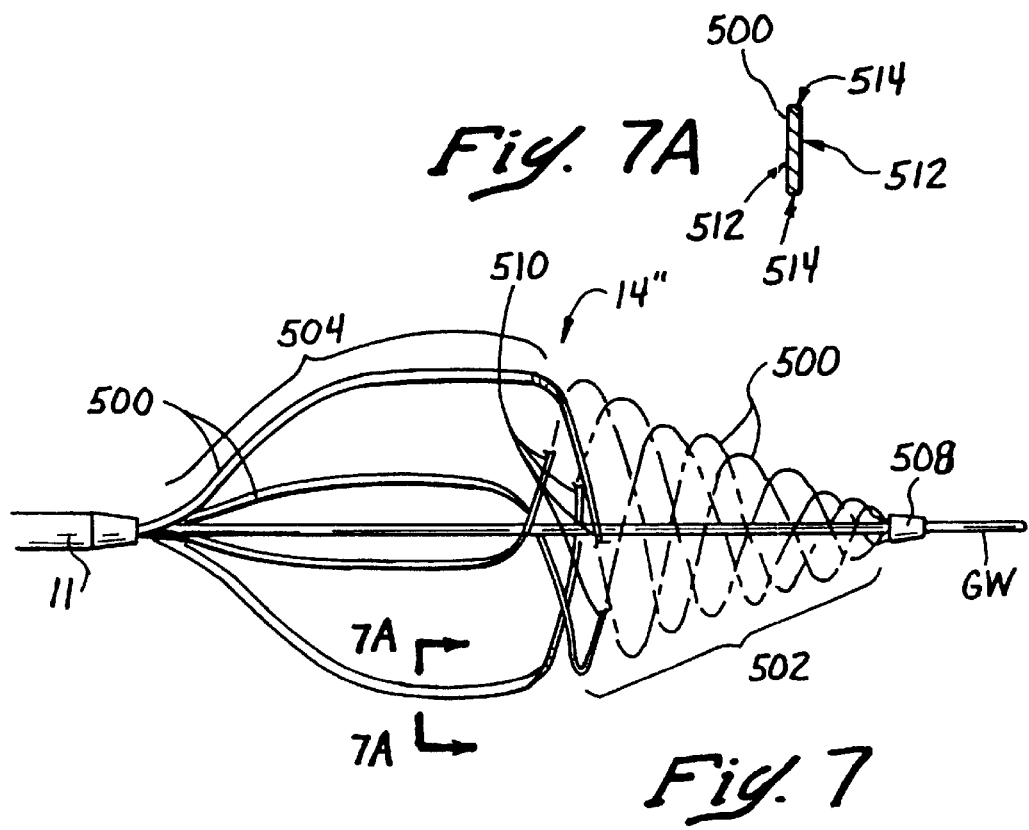

EMBOLECTOMY CATHETERS AND METHODS FOR TREATING STROKE AND OTHER SMALL VESSEL THROMBOEMBOLIC DISORDERS

FIELD OF THE INVENTION

The present invention relates generally to medical methods and devices, and more particularly to thrombolectomy catheters, and methods for using such thrombolectomy catheters, for removing blood clots or other matter from the lumens of blood vessels or other anatomical conduits.

BACKGROUND OF THE INVENTION

Various types of thromboembolic disorders, such as stroke, pulmonary embolism, peripheral thrombosis, atherosclerosis, and the like, are known to occur in human beings and other mammals. Such thromboembolic disorders are typically characterized by the presence of a thromboembolus (i.e., a viscoelastic blood clot comprised of platelets, fibrinogen and other clotting proteins) which has become lodged at a specific location in a blood vessel.

In cases where the thromboembolism is located in a vein, the obstruction created by the thromboembolus may give rise to a condition of blood stasis, with the development of a condition known as thrombophlebitis within the vein. Moreover, peripheral venous embolisms may migrate to other areas of the body where even more serious untoward effects can result. For example, the majority of pulmonary embolisms are caused by emboli that originate in the peripheral venous system, and which subsequently migrate through the venous vasculature and become lodged with the lung.

In cases where the thromboembolus is located within an artery, the normal flow of arterial blood may be blocked or disrupted, and tissue ischemia (lack of available oxygen and nutrients required by the tissue) may develop. In such cases, if the thromboembolism is not relieved, the ischemic tissue may become infarcted (i.e., necrotic). Depending on the type and location of the arterial thromboembolus, such tissue infarction can result in death and amputation of a limb, myocardial infarction, or stroke. Notably, strokes caused by thromboemboli which become lodged in the small blood vessels of the brain continue to be a leading cause of death and disability, throughout the world.

In modern medical practice, thromboembolic disorders are typically treated by one or more of the following treatment modalities:

a) pharmacologic treatment wherein thrombolytic agents (e.g., streptokinase, urokinase, tissue plasminogen activator (TPA)) and/or anticoagulant drugs (e.g., heparin, warfarin) are administered in an effort to dissolve and prevent further growth of the clot;

b) open surgical procedures (e.g., surgical embolectomy or clot removal) wherein an incision is made in the blood vessel in which the clot is lodged and the clot is removed through such incision-sometimes with the aid of a balloon-tipped catheter (e.g., a "Fogarty Catheter") which is passed through the incision and into the lumen of the blood vessel where its balloon is inflated and used to extract the clot out of the incision; and, c) transluminal catheter-based interventional procedures wherein a clot removing/disrupting catheter (e.g., a suction-type catheter having a suction tip, clot-capturing type catheter having a clot capturing receptacle (e.g., a basket, coil, hook, etc.), or clot-disrupting catheter having a clot disrupting apparatus (e.g., an ultrasound probe or laser)) is percutaneously inserted and advanced through the patient's vasculature to a location adjacent the clot. The suction tip, clot capturing receptacle or clot disrupting apparatus is used to aspirate, capture & remove, disrupt or ablate the offending clot.

Each of the above-listed treatment modalities has its own set of advantages and disadvantages. For example, pharmacologic treatment has the advantage of being non-invasive and is often effective in lysing or dissolving the clot. However, the thrombolytic and/or anticoagulant drugs used in these pharmacologic treatments can cause untoward side effects such as bleeding or hemorrhage. Also, in cases where time is of the essence, such as cases where an arterial thromboembolism is causing severe tissue ischemia (e.g., an evolving stroke or an evolving myocardial infarction) the time which may be required for the thrombolytic drugs to fully lyse or dissolve the blood clot and restore arterial blood flow may be too long to avoid or minimize the impending infarction.

Open surgical thrombus-removing procedures can, in many cases, be used to rapidly remove clots from the lumens of blood vessels, but such open surgical procedures are notoriously invasive, often require general anesthesia, and the use of such open surgical procedures is generally limited to blood vessels which are located in surgically accessible areas of the body. For example, many patients suffer strokes due to the lodging of blood clots in small arteries located in surgically inaccessible areas of their brains and, thus, are not candidates for open surgical treatment.

Transluminal, catheter-based interventional procedures are minimally invasive, can often be performed without general anesthesia, and can in some cases be used to rapidly remove a clot from the lumen of a blood vessel. However, such catheter-based interventional procedures are highly operator-skill-dependent, and can be difficult or impossible to perform in small or tortuous blood vessels. Thus, patients who suffer strokes due to the presence of clots in the small, tortuous arteries of their brains may not presently be candidates for catheter-based, transluminal removal of the clot, due to the small size and tortuosity of the arteries in which their clots are located.

In concept, the trasluminally deployable clot capturing type of catheters could be useable in ischemic strokes, because they are typically capable of removing an offending blood clot without the need for suction or application of energy (e.g., laser, ultrasound) which could be injurious to the delicate, small blood vessels of the brain. However, none of the prior art trasluminally deployable clot capturing type of catheters are believed to be of optimal design for use in the small blood vessels of the brain because they are a) not equipped with appropriate guidewire passage lumens to allow them to be passed over previously inserted, small-diameter (e.g., 0.006–0.018 inch) guidewires, b) they are not adapted for rapid exchange over a guidewire of standard length (e.g., a guidewire which is less than twice the length of the catheter) and c) the clot capturing receptacles of these catheters are not optimally constructed and configured for removal of clots from very small blood vessels as are typically found in the brain.

Examples of translumally deployable clot-capturing type embolectomy catheters of the prior art include those described in U.S. Pat. No. 4,706,671 (Weinrib), U.S. Pat. No. 4,873,978 (Ginsburg), U.S. Pat. No. 5,011,488 (Ginsburg) and PCT International Patent Publication No.

WO 97/27808 (Wensel, et al.). However, for the reasons stated above and/or other reasons, none of these prior art embolectomy catheters are believed to be optimally designed for treating ischemic stroke.

Thus, there exists a need for the development of new transluminally insertable, clot-capturing type embolectomy catheters which are advanceable and exchangeable over pre-inserted small diameter guidewires, and which are constructed to rapidly and selectively remove blood clots or other matter from small, delicate blood vessels of the brain, so as to provide an effective treatment for evolving strokes and other thromboembolic disorders.

SUMMARY OF THE INVENTION

The present invention generally comprises an embolectomy catheter device and method for removing blood clots or other matter from the lumens of blood vessels or other anatomical conduits of a mammalian body. The embolectomy catheters and methods of the present invention are particularly suitable for use in removing clots or thromboemboli from small arteries of the mammalian brain to prevent or minimize the severity of stroke.

A. Embolectomy Catheters of the Present Invention

An embolectomy catheter device of the present invention generally comprises; a) an elongate, pliable clot penetrating catheter which is advanceable, distal end first, through the clot or other obstructive matter (e.g., thrombus, thromboembolus, peices of detached atherosclerotic plaque, foreign matter, etc.) which is to be removed, and b) a matter capturing receptacle which is deployable from the distal end of the catheter after it has been advanced through the obstructive matter, to capture and facilitate removal of the obstructive matter. The matter capturing receptacle is initially disposable in a first or stowed configuration wherein the receptacle is in a radially collapsed condition and contained upon or within the catheter or otherwise sufficiently compact to pass through the clot or other obstructive matter. Thereafter, the matter capturing receptacle is deployable (e.g., advanceable, projectable and/or expandable) from the catheter such that it assumes a second or expanded configuration wherein the receptacle may receive and at least partially surround the distal aspect of the clot or other obstructive matter so as to facilitate extraction and removal of the blood clot or other obstructive matter along with the catheter.

A guidewire lumen may extend longitudinally through the entire length of the catheter (i.e., an "over-the-wire" embodiment) or through only a distal portion of the catheter or through an attached guidewire receiving loop/projection (i.e., a "rapid exchange" embodiment). In either of these embodiments of the catheter, the guidewire lumen may extend through the matter capturing receptacle such that the catheter (with its matter capturing receptacle in its collapsed or stowed configuration) may be advanced over a guidewire which has previously been passed through the vessel-obstructing clot or other obstructive matter. Such arrangement of the guidewire lumen additionally allows the embolectomy catheter to be exchanged (e.g., removed and replaced with another embolectomy catheter or another type of catheter) if such exchange should become necessary or desirable. This ability to allow the guidewire to remain positioned through the offending clot or other obstructive matter may serve to ensure that the catheter or its replacement can be re-advanced through the clot or other obstructive matter to its desired position.

The matter capturing receptacle of the catheter may comprise a distal obstructive matter-engaging portion (e.g., a coil, basket or concave member) of porous construction (e.g., a woven, coiled or mesh structure formed of wire, fiber or fabric), which is attached to the catheter by way of one or more proximal struts (e.g. connector members (e.g., a plurality of thin wires or struts). Initially, with the matter capturing receptacle disposed in its first (e.g., collapsed or stowed) configuration, the distal end of the catheter is advanced through the clot or other obstructive matter. After the catheter has been advanced through the clot or other obstructive matter, the matter capturing receptacle is moved to its second (e.g., expanded or operative) configuration, such that the distal obstructive matter-engaging portion 16 of the receptacle will contact and/or at least partially surround the distal aspect of the clot or other obstructive matter. The distal obstructive matter-engaging portion of the receptacle is preferably of permeable construction to permit blood to flow therethrough, but is sufficiently dense (i.e., sufficiently impermeable) to prevent the clot or other obstructive matter from passing therethrough. In this manner, the distal obstructive matter-engaging portion of the receptacle is useable to retract or draw the clot or other obstructive matter, in the proximal direction, from its then-present location. The proximal strut(s) which extend between the receptacle to the catheter are typically of radially splayed or outwardly angled configuration and is/are preferably configured, oriented and positioned so as to slice, cut or otherwise pass through the matter of the clot or other obstructive matter, when deployed at a site distal to the clot or other obstructive matter and subsequently retracted in the proximal direction. To assist such proximal strut(s) in passing through the clot or other obstructive matter, energy (e.g., radio-frequency energy, vibration, heat, etc) may be applied to the proximal strut(s) during their proximal retraction through the clot or other obstructive matter.

A contrast medium injection port may be formed on the proximal portion of the embolectomy catheter, to allow radiographic contrast medium (e.g., dye) to be injected through the catheter while a guidewire remains positioned within the guidewire lumen.

B. Rapid Exchange Microcatheter Useable in Conjunction with Embolectomy Catheters of the Present Invention Further in accordance with the present invention, there is provided a rapid exchange microcatheter which comprises a small diameter flexible microcatheter of a type commonly used in neuroradiology procedures (e.g., Prowler™ microcatheter, Cordis Endovascular Systems, Miami Lakes, Fla.), which has greater flexibility at or near its distal end than at or near its proximal end, and which includes in accordance with this invention, the addition of a guidewire passage port formed in the sidewall of the catheter, at a spaced distance (e.g., 0.5–35 cm) from its distal tip. (Alternatively, a guidewire receiving loop or projection may be formed in the side of the catheter body.) A guidewire deflector may be formed within the main lumen of the catheter adjacent to the guidewire passage aperture, to deflect the proximal end of a guidewire out of the guidewire passage aperture as the catheter is advanced over the guidewire. The formation of such guidewire passage aperture and guidewire deflector allows a guidewire to be passed through only a distal portion of the catheter lumen. This lumen arrangement allows the microcatheter to be exchanged (i.e., removed and replaced by another microcatheter or an embolectomy catheter of the above-summarized design) while the operator holds the guidewire in place by grasping the exteriorized proximal end of the guidewire—even in instances where a standard length guidewire (i.e., not an "exchange-length" guidewire) is used.

C. Methods of the Present Invention for Removing Clots or Other Matter from Blood Vessels Further in accordance with the present invention, there are provided a method for treating ischemic stroke caused by a thromboembolism which has become lodged in a small blood vessel of the brain (i.e., blood vessels located in, on or around the brain). The method of the present invention may be carried out using the rapid-exchange microcatheters and embolectomy catheters of the present invention. The preferred method generally comprises the steps of:

A. percutaneously inserting a guidewire (alone or in combination with a guide catheter) into an intracranial blood vessel, using the Seldinger technique or other appropriate method of percutaneous guidewire placement;

B. advancing a microcatheter over the guidewire, or separately from the guidewire, through the vasculature until the microcatheter is near the site at which the blood clot or other obstructive matter is located;

C. passing radiographic contrast medium (e.g., dye) through the microcatheter under radiographic visualization to verify the exact location of the obstructive matter and/or to map the vascular anatomy in the area of the obstruction;

D. advancing the guidewire (or a separate small guidewire) through the microcatheter until such guidewire becomes located in a desired operative position relative to the obstructive matter (e.g., such that its distal end has fully or partially traversed or passed through the thromboembolism or other obstructive matter);

E. withdrawing and removing the microcatheter while substantially maintaining the small guidewire in its operative position (e.g., preventing the guidewire from moving so far as to lose the access to the obstructive matter that the presence of the guidewire provides);

F. advancing a matter-capturing type embolectomy catheter (such as an embolectomy catheter of the present invention) which has an obstructive matter-capturing receptacle deployable therefrom, over the operatively positioned guidewire until the distal end of the embolectomy catheter has advanced fully or at least partially through the obstructive matter (e.g., has penetrated through an obstructive thromboembolism);

G. optionally injecting radiographic contrast medium through a lumen of the embolectomy catheter to guide or verify the positioning of the embolectomy catheter relative to the lodged blood clot or other obstructive matter;

H. deploying the obstructive matter-capturing receptacle of the embolectomy catheter such that it assumes its second or expanded configuration at a site which is distal (i.e., downstream) of the lodged blood clot or other obstructive matter;

I. retracting the obstructive matter-capturing receptacle such that a proximal portion of the receptacle (i.e., proximal struts) passes through the thromboembolism and at least a portion of the clot or other obstructive matter becomes located within the obstructive matter-receiving portion of the obstructive matter-capturing receptacle;

J. optionally injecting radiographic contrast medium through a lumen of the embolectomy catheter to determine whether blood flow has been restored through the region of the blood vessel which had previously been deprived of blood flow due to the presence of the clot or other obstructive matter; and, k. retracting the embolectomy catheter to remove the blood clot or other obstructive matter from the body (e.g., withdrawing the embolectomy catheter and the extracted clot or other obstructive matter through the percutaneous entry tract through which the catheter had previously been inserted.

Thus, by the above-summarized method of the present intention, the blood clot or other obstructive matter which is causing an ischemic (i.e., thrombotic or embolic) stroke is removed and arterial bloodflow is restored to the region of the brain which had become ischemic due to the lodging on the offending blood clot or other obstructive matter within the blood vessel.

Further elements, objects and advantages of the present invention will become apparent to those of skill in the art upon reading and understanding of the following detailed description of preferred embodiments and consideration of the accompanying drawings.

BRIEF DESCRIPTION OF THE DRAWINGS

FIG. 1 is a perspective view of a human patient having a first embodiment (an "over-the-wire embodiment) of an embolectomy catheter of the present FIG. 1a is a perspective view of the embolectomy catheter device of FIG. 1 operatively positioned upon a guidewire, and having its obstructive matter-capturing receptacle disposed in an expanded configuration.

FIG. 2a is an enlarged longitudinal sectional view of the distal end of the over-the-wire embolectomy catheter of FIG. 1 with its obstructive matter-capturing receptacle in a first or stowed position.

FIG. 2b is an enlarged, broken, longitudinal sectional view of the distal end of the over-the-wire embolectomy catheter of FIG. 1 with its obstructive matter-retrieving member in a distally advanced position and its obstructive matter-capturing receptacle disposed in a fully expanded configuration.

FIG. 2c is a cross-sectional view through line 2c—2c of FIG. 2a.

FIG. 2d is a cross-sectional view through line 2d—2d of FIG. 2a.

FIG. 2d' is a cross-sectional view through line 2d—2d of FIG. 2a, modified to show an alternative mode of constructing the guide bores in the distal tip member, through which the wires which form the obstructive matter-capturing receptacle extend.

FIG. 3a is an enlarged, broken, longitudinal sectional view of the distal end of the over-the-wire microcatheter of the prior art.

FIG. 3b is an enlarged, broken, longitudinal sectional view of the distal end of a second embodiment (i.e., another over-the-wire embodiment) of an embolectomy catheter of the present invention.

FIG. 3b' is a cross-sectional view through line 3b'—3b' of FIG. 3b.

FIG. 3c is an enlarged, broken, longitudinal sectional view of the distal end of a rapid exchange microcatheter of the present invention.

FIG. 3c' is a cross-sectional view through line 3c'—3c' of FIG. 3c.

FIG. 3d' is a cross-sectional view through line 3d'—3d' of FIG. 3d.

FIG. 3e is an enlarged, longitudinal sectional view of the distal end of a fourth embodiment (i.e., another rapid exchange embodiment) of an embolectomy catheter of the present invention.

FIG. 3e' is a cross-sectional view through line 3e'—3e' of FIG. 3e.

FIG. 3f is an enlarged, longitudinal sectional view of the distal end of a fifth embodiment (i.e., another rapid exchange embodiment) of an embolectomy catheter of the present invention.

FIG. 3f' is a cross-sectional view through line 3f'—3f' of FIG. 3f.

FIG. 4 is a perspective view of the third embodiment (i.e., a rapid exchange embodiment) of an embolectomy catheter of FIG. 3d having a guidewire operatively inserted through its guidewire lumen and its obstructive matter-capturing receptacle in its deployed, radially expanded position.

FIG. 5 is a perspective view of a first alternative obstructive matter-capturing receptacle which may be incorporated into any of the embolectomy catheters of the present invention.

FIG. 5' is an enlarged view of portion 5' of FIG. 5.

FIG. 5" shows an alternative construction for portion 5' of FIG. 5.

FIG. 5a is a distal end view of FIG. 5.

FIG. 5b is a perspective view of a second alternative obstructive matter-capturing receptacle which may be incorporated into any of the embolectomy catheters of the present invention.

FIG. 5b' is a perspective view of the second alternative obstructive matter-capturing receptacle of FIG. 5b having a clot captured therewithin and with its support spines being partially retracted into the catheter.

FIG. 5b" is a perspective view of the second alternative obstructive matter-capturing receptacle of FIG. 5b having a clot captured therewithin and with its support spines being further retracted into the catheter so that the obstructive matter capturing receptacle is drawn partially around the captured clot.

FIG. 5c is a perspective view of a third alternative obstructive matter-capturing receptacle which may be incorporated into any of the embolectomy catheters of the present invention.

FIG. 6 is a perspective view of an optional guide catheter of the present invention having a proximal obstructive matter containment apparatus operatively deployed therefrom, and an embolectomy catheter of the present invention operatively inserted therethrough.

FIG. 7 is an elevational view of a variant of the helical basket type obstructive matter capturing receptacle of the catheters shown in FIGS. 1, 2b and 4, such variant being constructed of metal ribbon rather than wire.

FIG. 7a is a cross-sectional view through line 7a—7a of FIG. 7, illustrating the manner in which the metal ribbons may be twisted to enhance the ability of the proximal strut portions to the obstructive matter capturing receptacle to cut through the thromboembolic material.

Figure 3D:
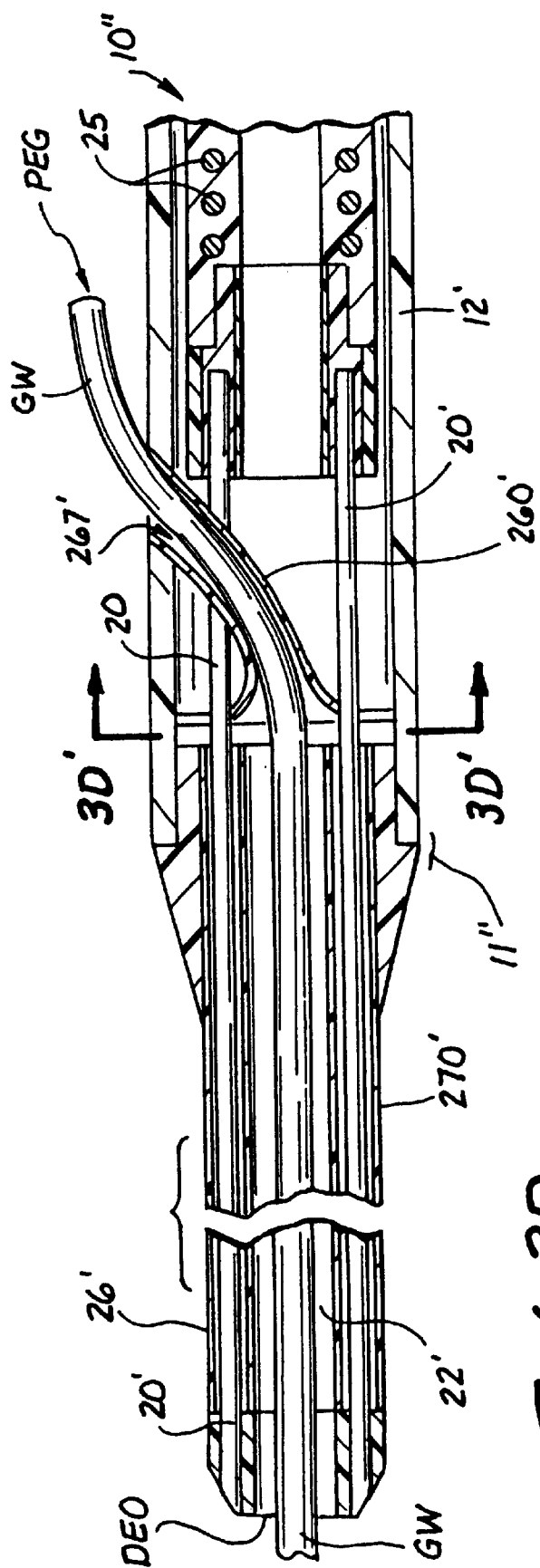
FIG. 3d is an enlarged, broken, longitudinal sectional view of the distal end of a third embodiment (i.e., a rapid exchange embodiment) of an embolectomy catheter of the present invention.
Figure 3D:
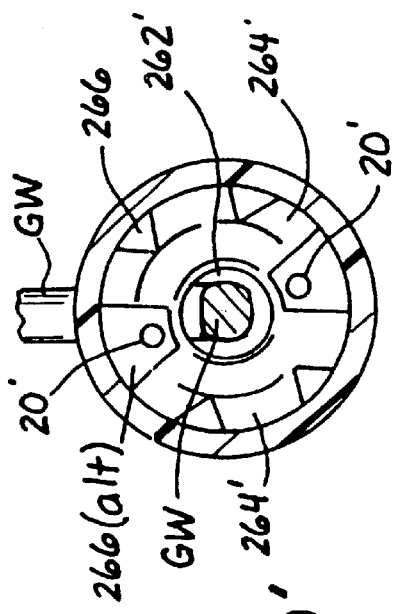

The particular embodiments shown in these drawings, and additional embodiments of the invention, may now be better understood by reading and understanding the following detailed description wherein specific reference is made to the structures and steps illustrated or shown in the drawings.

DETAILED DESCRIPTION OF THE INVENTION

A. Over-the Wire Embodiments of the Embolectomy Catheter Device

Referring now to the drawings, wherein the showings are for the purpose of describing and illustrating exemplary embodiments of the present invention, and not for the purpose of limiting the scope of the invention, FIG. 1 shows a human patient in whom an over the wire embodiment of the embolectomy catheter device 10 of the present invention has been inserted for the purpose of removing a thromboembolus or blood clot from a small artery located in the patient's brain. Prior to introduction of the catheter device 10 the offending clot had been located by angiography or other imaging means, and a small (e.g., 0.006–0.010 inch outer diameter) guidewire GW was inserted into the patient's femoral artery and advanced into the artery of the brain in which the clot is located and at least partially through the clot. Thereafter, the catheter device 10 was advanced over the previously inserted guidewire GW to a position where the distal end of the catheter device 10 is near the clot.

First Embodiment

As shown in FIGS. 1–2e, the first embodiment of the over-the-wire catheter device 10 comprises an elongate, pliable catheter 11 having a clot capturing receptacle 14 deployable from its distal end DE, as shown. The obstructive matter-capturing receptacle 14 is formed of a plurality (e.g., 2 or more) wire members 20 which are initially retractable to substantially straight configurations and a first (i.e., stowed) position, within the catheter 11. (See FIG. 2a) When it is desired to deploy the obstructive matter capturing receptacle 14, the preformed wire members 20 are advanced in the distal direction such that the emerge from the constraint of the catheter 11 and resiliently assume a second (i.e. operative) configuration wherein the distal portions of the wire members form a helical basket 16 having an open proximal mouth or rim 17, as shown in FIG. 2b. When in such operative configuration (FIG. 2b), the helical basket 16 is sufficiently porous to allow blood to flow therethrough, but sufficiently dense to engage and withdraw in the proximal direction, a thromboembolism. A nose cone 30 is positioned on the distal ends of the wire members 18. The proximal portions 18 of the elongate wire members 20 act as connecting members between the helical basket 16 and the catheter 11. These proximal portions 18 of the wire members 20 are of sufficiently small diameter or are otherwise configured to be retracted through a thromboembolism, without causing substantial disruption or segmentation of the thromboembolism. In some embodiments energy (e.g. heat, vibration, etc) may be applied to the proximal portions 18 of the wire members 20 to facilitate their retraction through the thromboembolic material without causing substantial disruption or segmentation of the thromboembolism.

The wire members 20 of which the capturing receptacle 14 is formed may be of any suitable material, such as elastic, superelastic or shape memory alloy wire. The distal portions of these wire members are preformed to the shape of the helical basket 16 but are sufficiently elastic to assume substantially straight configurations when retracted through the guide bores 26 and into the catheter 11 and maintained in a taut state under a small amount of proximally directed pressure. (See FIG. 2a) However, when these preformed wire members are extended or advanced through the guide bores 26 and out of the distal end DE of the catheter 11, and relieved of the surrounding restraint of the catheter 11 and the proximally-directed tension, they will resiliently self-coil into the generally frustoconical shape of the helical basket 16.

To facilitate the desired advancement and retraction of these preformed wire members 20, the proximal ends of these members 20 are attached to the distal end of a longitudinally slidable actuator 24 which is positioned within the lumen 22 of the catheter body 12. A hollow actuator lumen 22a extends through the actuator 24 and is in axial alignment with the lumen 22 of the catheter body 12. The shaft of the actuator 24 has a wire braid or coil 25 formed therein to impart stiffness and strength. A distal tip member 28 is formed on the distal end DE of the catheter body 12, such distal tip member 28 having a hollow tip member lumen 22TM which extends longitudinally through the center thereof, and four (4) wire passage bores 26 which also extending longitudinally therethrough, at radially spaced-apart locations (i.e., the 3, 6, 9 and 12 o'clock positions). The distal tip member 28 may be formed of material which is more rigid than the catheter body 12 and may have a proximal portion 40 of reduced diameter which is inserted into the distal end DE of the catheter body lumen 22, as shown in FIGS. 2a, 2b and 2d. Each of the four (4) preformed segments 20 which form the obstructive matter capturing receptacle 14, when advanced out of the catheter 11 must pass through a respective one of the wire passage bores 26 formed in the catheter tip member 28. FIG. 2d' shows an alternative construction of the distal tip member wherein four (4) cut-out notches 26A,T are formed at the 3, 6, 9 and 12 o'clock positions to serve as discrete guide wire passageways for the individual wire segments 20, in lieu of the wire passage bores 26.

A proximal actuator shaft 24' extends to a housing 13 formed on the proximal end of the catheter, and such proximal actuator shaft 24' may be manually advanced and retracted to control deployment and retraction of the obstructive matter capturing receptacle 14. A contrast medium injection port 15 is also formed on the proximal housing 13, for injection of radiographic contrast medium through the lumen 22 and out of the distal end DE of the catheter 11. In this regard, it is preferable that the outer diameter of the guidewire GW be at least slightly less than the inner diameter of the lumen 22 to permit some radiographic contrast medium to pass through the lumen 22 and out of the distal end of the catheter even when the guidewire is positioned within the lumen. Also, radiographic contrast solutions (i.e., dyes) of minimal viscosity may be selected to enhance the ability of the contrast medium to pass through the lumen 22 while the guidewire GW is positioned therewithin.

When the actuator 24 is withdrawn in the proximal direction, it will pull the wire segments 20 in the proximal direction, through the wire passage bores 26 and into the lumen 22 of the catheter. When the actuator 24 is fully retracted, as shown in FIG. 2a, the segments 20 will be drawn fully through the wire passage bores 26 and will assume substantially straight configurations, and the nose cone 30 mounted on the distal end of the obstructive matter capturing receptacle will be in direct abutment with the catheter tip member 28 such that the hollow nose cone lumen 22NC is in axial alignment with the distal tip lumen 22DT and the lumen 22 of the catheter body 12.

Second Embodiment

FIGS. 3b and 3b' show a second embodiment of an over-the-wire catheter device 10' which differs from the first embodiment 10 in several ways. For example, the obstructive matter-capturing receptacle (not shown) of this second embodiment is formed by only two (2) wire members 20' instead of four (4) as in the first embodiment 10. Also, the catheter 11' of this second embodiment incorporates an elongate distal segment 270 of reduced diameter and increased flexibility—similar to that of the commercially available microcatheters (e.g., Prowler™ microcatheter, Cordis Endovascular Systems, Miami Lakes, Fla.), an example of which is shown in FIG. 3a and generally comprises a proximal portion PP having a lumen L and a distal segment 270 having a lumen 271 which is continuous with the lumen L of the proximal portion PP.

With specific reference to FIGS. 3b and 3b', this second embodiment of the over the wire embolectomy catheter device 10' comprises an elongate, pliable catheter 11' having a helical basket type obstructive matter capturing receptacle (not shown)similar to that of the first embodiment, but wherein the receptacle (not shown) is formed of only two (2) wire members. As in the above described first embodiment, the obstructive matter capturing receptacle (not shown) of this second embodiment 10' is initially retractable to a first (i.e., stowed) configuration and is subsequently advanceable to second (i.e. operative) configuration which is essentially the same as that described above with respect to the first embodiment 10.

In this second embodiment, the flexible catheter 11' comprises a proximal portion 12' having a first diameter and first flexibility, and a distal portion 270 which has a second (i.e., smaller) diameter and a second (i.e., greater) flexibility. An insert member 28' having four (4) guide bores 26' extending longitudinally therethrough, is positioned within the lumen 271' of, and is coextensive with, the distal portion 270 of the catheter 11'. This insert member 28' is a generally cylindrical member having four (4) longitudinal bores 20' extending therethrough, as shown in FIG. 3b'. However, since the obstructive matter capturing receptacle (not shown) of this embodiment is formed of only two (2) elongate members 20', the remaining two guide bores 26' remain unoccupied and may serve as passageways through which radiographic contrast medium (e.g., dye), medicaments, perfusion solution or other fluid my flow.

B. Rapid Exchange Embodiments of the Embolectomy Catheter Device

FIGS. 3d, 3d', 3e, 3e', 3f', 3f' and 4 are illustrative of rapid exchange embodiments of the embolectomy catheter device 10", 10''' and 10''''. These rapid exchange embolectomy catheter devices 10", 10''' and 10'''' incorporate guidewire lumens which extend through only a distal portion of the catheter 11", 11''', 11'''' so as to permit the catheter 11", 11''', 11'''' to be exchanged without the need for use of an exchange-length guidewire (i.e., a guidewire which is long enough to allow the exteriorized portion of the guidewire to be longer than the catheter so that the catheter may be withdrawn, removed and exchanged while holding the guidewire in substantially fixed position. These rapid-exchange embodiments are particularly suited for the treatment of stroke by removing thromboemboli from small blood vessels of the brain (i.e., blood vessels located on, in or around the brain), as the use of exchange-length guidewires may be undesirable in such delicate neuroradiological procedures. see, Morris, P., *Practical Neuroradiology*, Chapter 2, page 41 (Williams & Wilkins 1997)

Third Embodiment

FIGS. 3d and 3d' show a third embodiment (i.e., a rapid exchange type embodiment) of the embolectomy catheter device 10" which is similar in construction to the above described second embodiment 10', but which incorporates a guidewire passage port 267' formed in the sidewall of the catheter 11" at a spaced distance (e.g., 0.5–35 cm) from its distal end, and a guidewire deflector tube 260' which extends from the guidewire passage port 267' to the lumen 22'. The guidewire deflector tube 260' has a flared distal end which is held in a centered position within the lumen by a plurality of radial support members 264'. Longitudinal passages 266, 266(alt) are formed between the radial support members 264' to allow radiographic contrast medium or other fluid to flow through the lumen 22', past the flared distal end of the guidewire deflector tube 260'. Selected ones of the longitudinal passages 266(alt) are larger than the others 266 to permit the elongate members 20' which form the obstructive matter capturing receptacle to pass therethrough, as shown. The proximal end of a guidewire PEG may be inserted into the distal end opening DEO of the catheter 11" and, thereafter, the catheter 11" may be advanced in the distal direction such that the proximal end of the guidewire PEG will enter the flared distal end of the guidewire deflector tube 260', and will be thereby deflected out of the side guidewire passage port 267', as shown.

Fourth Embodiment

In the fourth embodiment (i.e., another rapid exchange embodiment) shown in FIGS. 3e and 3e', the catheter 11'" comprises a main tube 300 which has a proximal portion 302 of a first diameter D1 and a distal portion 304 of a second diameter D2. A side tube 308 is affixed to one side of the distal portion 304 of the main tube 300, and a guidewire passage aperture 310 is formed into the lumen 309 of the side tube 308, such that the lumen 309 of the side tube may be used as the guidewire lumen, and the distal portion of the guidewire GW which emerges from the side tube lumen 309 may then be passed through the separate guidewire lumen of the obstructive matter capturing receptacle 22 (not shown in FIG. 3e) and/or any nose cone lumen 22NC (not shown in FIG. 3e), as described fully hereabove.

Fifth Embodiment

The fifth embodiment (i.e., another rapid exchange embodiment) of the embolectomy catheter device 10"" is similar in construction and operates in the same manner as the fourth embodiment 10'" described above, except that the main tube 300' of this fifth embodiment 10"" is formed of a continuous wire 316 which is would in a tight helical coil, as shown. This construction of the main tube 300' may provide enhanced flexibility over other forms of construction.

C. Alternative Components and Optional Elements Which May be Incorporated into any Embodiment of the Embolectomy Catheter Devices

1. Alternative Types of Obstructive matter Capturing Receptacles

The embolectomy catheter devices 10, 10', 10", 10'", 10"" of the present invention may incorporate various types of obstructive matter capturing receptacles as alternatives to the helical wire basket type receptacles 14, 14' shown in FIGS. 1a, 2b and 4. In particular, several alternative obstructive matter capturing receptacles are shown in FIGS. 5–7.

FIGS. 5–5a show one alternative obstructive matter-capturing receptacle 400 which comprises a plurality of elastic or superelastic wire spokes 402 which are preformed to a radially splayed configuration as shown, and which have a membranous or fabric cover 404 disposed thereon to form an umbrella like structure. The membranous or fabric cover 404 may be of non-porous or porous configuration, and is preferably formed of material such as polyethylene, polytetrafluoroethylene, polyurethane, ethylene vinyl acetate or silicone. A central hub is formed at the center of the spokes 402, and a guidewire lumen extends through such central hub such that the guidewire may pass the center of the receptacle 400, in the manner depicted in FIGS. 5 and 5a. The ends of the spokes 402 may have bulbs 408 formed thereon to minimize trauma to the surrounding blood vessel walls, as shown in FIG. 5'. Or, as an alternative to such bulbs 408, atraumatic loops 410 may be formed on the distal ends of the spokes 402 to prevent vascular trauma. The spokes 402 are of sufficiently small diameter to be retracted through a thromboembolism without causing substantial disruption of segmentation of the thromboembolism. Also, in the embodiment shown in FIG. 5, it will be appreciated that the spokes 402 may have a greater curvature than that shown, such that the free ends of the spokes 402 will not be in direct contact with the blood vessel wall.

FIGS. 5b–5b" show another obstructive matter capturing receptacle 420 which comprises a plurality of elastic or superelastic wire spokes 402' which are pre-formed to a radially splayed configuration as shown, and a porous fabric (e.g., woven, knitted, mesh or net fabric) sac 422 attached to the spokes 402' to form an umbrella-like structure, as shown. The material used to form this sac 422 may be the same microporous material as specified hereabove with respect to the membranous or fabric cover 404 of the embodiment shown in FIG. 5. A central aperture 426 is formed in the sac 422 such that a guidewire GW may be passed through a region among the spokes 402', and through such aperture 426, as shown in FIGS. 5b and 5b'. Draw lines 424 are attached to the free ends of the spokes 402' and extend through the lumen of the catheter. These draw lines 424 and the spokes 402' are of sufficiently small diameter to be retracted through a thromboembolism without causing substantial disruption or segmentation of the thromboembolism. After the receptacle 420 has been advanced through the thromboembolism, it is deployed (e.g., radially expanded) and retracted such that the draw lines 424 and spokes 402' will retract through and will become located proximal to, the thromboembolism. Thereafter, the draw lines 424 are retractable into the catheter to pull distal ends of the spokes 402' inwardly such that the proximal mouth PM of the sac will be drawn partially around the captured obstructive matter in the manner shown in FIGS. 5b' and 5b".

FIG. 5c shows another alternative obstructive matter capturing receptacle which employs a resilient, generally football shaped cage to effect radial expansion/contraction of a membranous or fabric cover 444. As shown, the cage comprises approximately six (6) elongate members 442 of preformed elastic, super-elastic or shape memory metal wire disposed longitudinally about a longitudinal axis LA, and having the membranous or fabric covering 444 disposed on the distal portions DP thereof. The distal ends DE of the elongate members 442 are attached to a nose cone 446 which has a guidewire passage lumen extending longitudinally therethrough. When retracted into the lumen of the catheter, the members 442 will radially compress to a diameter which is received within the catheter lumen. However, when advanced out of the catheter the members 442 will resiliently expand to the configuration shown. The proximal portions of the members are sufficiently small in diameter to slice, cut or otherwise pass in the proximal direction through a thromboembolism or clot without disrupting or causing fragmentation of the thromboembolism or clot.

FIGS. 7 and 7a show an alternative helical basket type of obstructive matter capturing receptacle 14" which is of the same general configuration, and operates in the same manner, as the helical basket type receptacles 14, 14' shown in FIGS. 1a and 4, but wherein the receptacle 14" is formed of a plurality of flat ribbons 500 formed of metal such as cobalt-chromium-nickel alloy (Elgiloy™, Elgiloy, Inc., Elgin, Ill.), a shape memory and/or super-elastic material such as nickel-titanium alloy, or other suitable metal or plastic. The distal portions of the flat ribbons 500 are preformed to helical configurations to form the helical basket 502. The proximal portions of the ribbons 500 serve as connector members 504 between the helical basket 502 and the catheter 11. Each ribbon 500 has first and second flat surfaces 512 and first and second edges 514. Each of the ribbons 500 is twisted 90 degrees at a point of transition 510 between the connector members 504 and the helical basket 502. This twisting of the ribbons causes a) the distal portions to be situated with their edges 514 in juxtaposition such that a thromboembolus contained within the helical basket 502 will rest upon the flat surfaces of the ribbons 500, and b) the proximal portions to be situated with their edges aimed in the proximal direction to facilitate retraction of the distal connector members 504 through the thromboembolus without causing the thromboembolus to be substantially fragmented or disrupted.

Optional Guide Catheter/Proximal Obstructive Matter Retaining Member

As illustrated in FIG. 6, it may be desirable to use the embolectomy catheter devices 10, 10', 10", 10''', 10'''' in conjunction with a guide catheter 50 through which the embolectomy catheter 11 may be advanced. When such guide catheter 50 id used, a proximal obstructive matter retaining member 52, such as a tubular sheath having a radially flared and splayable distal end as shown in FIG. 5a, may be advanced out of the distal end DE of the guide catheter 50 such that the clot C or other obstructive matter may be captured between the distal obstructive matter receiving portion 16 of the receptacle 14 and the flared distal end of the proximal obstructive matter retaining member 52. The use of this optional proximal obstructive matter retaining member 52 may be particularly useful in cases where the thromboembolism is very fresh or has been inadvertently severed or segmented so as to present a danger of breaking apart or fragmenting during the removal procedure.

D. Rapid Exchange Microcatheter Useable in Conjunction with the Embolectomy Catheters In many procedures wherein the embolectomy catheters of this invention are used to remove thromboemboli from small blood vessels of the brain, it will be desirable to initially perform an angiogram of the blood vessel wherein the thromboembolism is believed to be located to a) verify the exact location of the thromboembolism and b) radiographically map the vascular anatomy in the immediate area of the thromboembolism and c) guide and verify the passage of a small guidewire through the offending thromboembolism. Because the embolectomy catheters 10, 10', 10", 10''', 10'''' of the present invention may necessarily be of very small diameter (e.g., 0.10–0.20 inches) in order to navigate the tiny blood vessels of the brain, the presence of the retracted obstructive matter capturing receptacle 14, 14', 400, 420 or 440 within that catheter 11 may severely limit the amount of radiographic contrast medium which could be infused though that catheter 11. Thus, in many instances, it may be desirable to initially insert a small angiography catheter (e.g., a microcatheter such as the Prowler™ microcatheter, Cordis Endovascular Systems, Miami Lakes, Fla.), an example of which is shown in FIG. 3a, into the obstructed blood vessel to perform the initial angiography and to accomplish precise positioning of the guidewire through the thromboembolism. After the initial angiography has been performed and the guidewire has been precisely positioned, the angiography catheter is withdrawn and removed, leaving the guidewire in place. Thereafter, an embolectomy catheter 10, 10', 10", 10''', 10'''' of the present invention is advanced over the pre-positioned guidewire to the location of the thromboembolism.

However, the microcatheters of the prior art have not been suitably designed for this novel procedure. Such microcatheters have heretofore of an "over-the-wire" type used primarily in procedures where the catheter is retracted and removed concurrently with the guidewire over which it was inserted. Thus, as those skilled in the art will appreciate, the prior art "over-the-wire" type microcatheters can only be exchanged over a stationary guidewire if the guidewire is an "exchange-length" wire or if an extension has been attached to the proximal end of the guidewire to permit the exchange. However, the use of such "exchange-length" guidewire or a guidewire extension may be contraindicated in procedures where the catheters are being inserted into and withdrawn from tiny delicate vessels of the brain. see, Morris, P., *Practical Neuroradiology*, Chapter 2, page 41 (Williams & Wilkins 1997)

In view of this shortcoming of the prior art microcatheters, applicant has devised the rapid-exchange microcatheter 265 shown in FIGS. 3c and 3c'. This rapid exchange microcatheter 265 comprises an elongate, flexible catheter having a proximal portion 12" of a first diameter and first flexibility, and a distal portion 270" which has a second (i.e., smaller) diameter and a second (i.e., greater) flexibility. A guidewire passage port 267 is formed in the sidewall of the catheter near the distal end of its proximal portion 12", and a guidewire deflector tube 260 extends from the guidewire passage port 267 to the lumen 271. The guidewire deflector tube 260 has a flared distal end which is held in a centered position within the lumen by a plurality of radial support members 264. Longitudinal passages 266 are formed between the radial support members 264 to allow radiographic contrast medium or other fluid to flow through the lumen 271, past the flared distal end of the guidewire deflector tube 260. The proximal end of a guidewire PEG may be inserted into the distal end opening DEO of the catheter and, thereafter, the catheter may be advanced in the distal direction such that the proximal end of the guidewire PEG will enter the flared distal end of the guidewire deflector tube 260, and will be thereby deflected out of the side guidewire passage port 267, as shown in FIG. 3c.

Figure 8A:
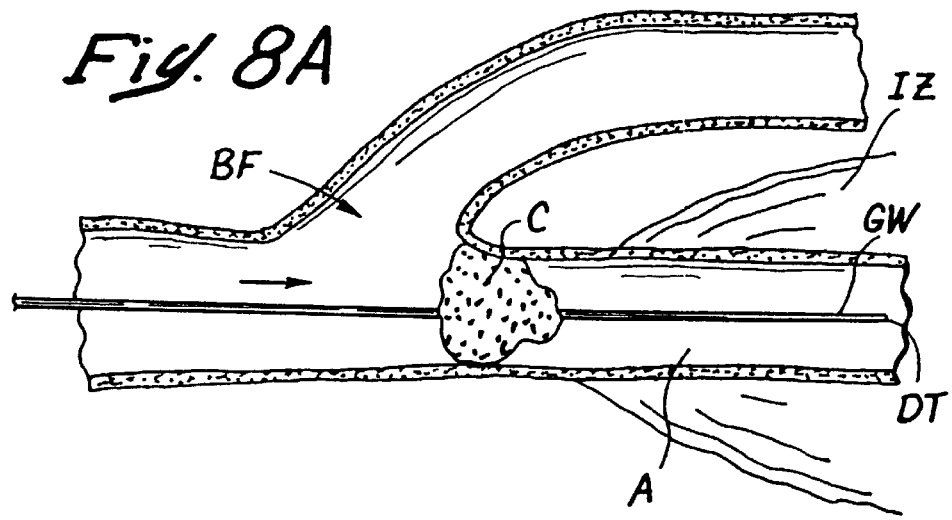
FIGS. 8a–8f are step-wise showings of a procedure wherein the first embodiment (i.e., an over-the-wire embodiment) of an embolectomy catheter of the present invention is used to remove a blood clot from a small blood vessel of a mammalian body.
Figure 8B:
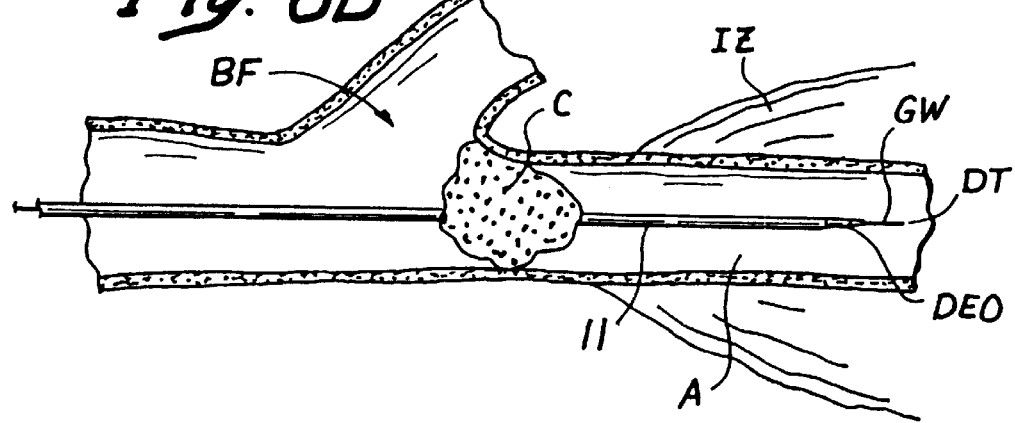
Figure 8C:
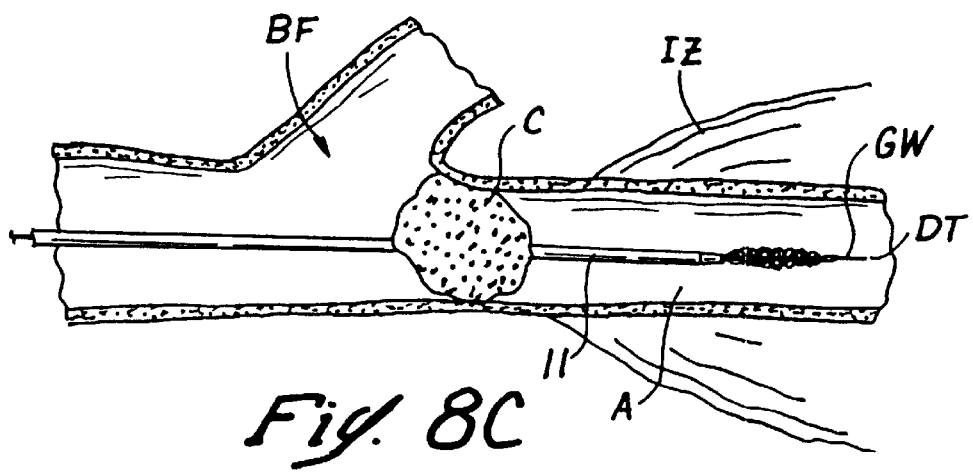
Figure 8D:
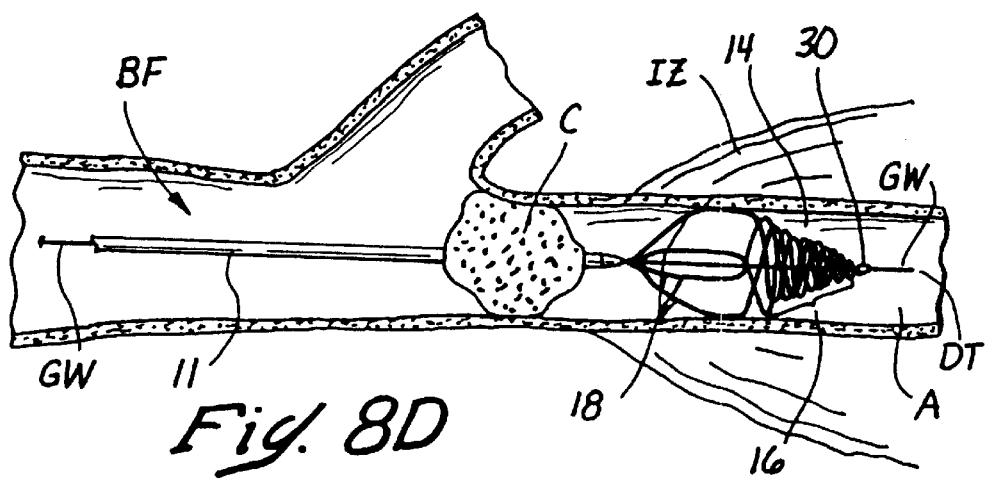
Figure 8E:
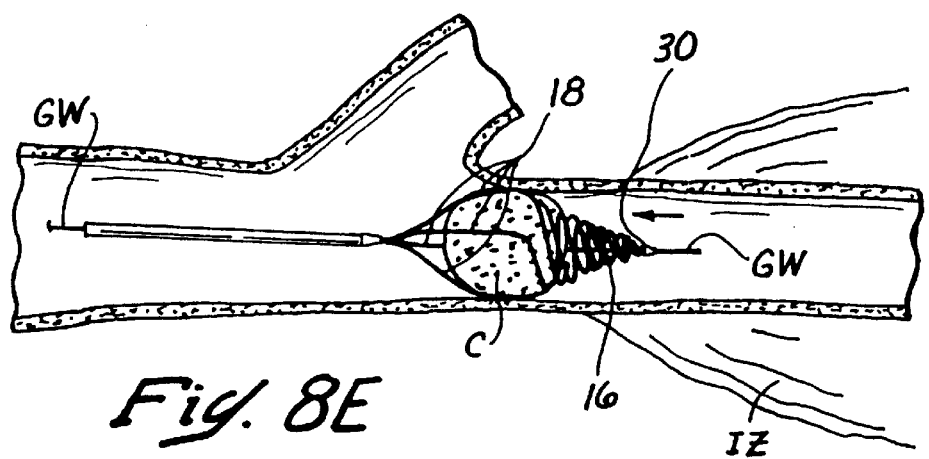
Figure 8F:
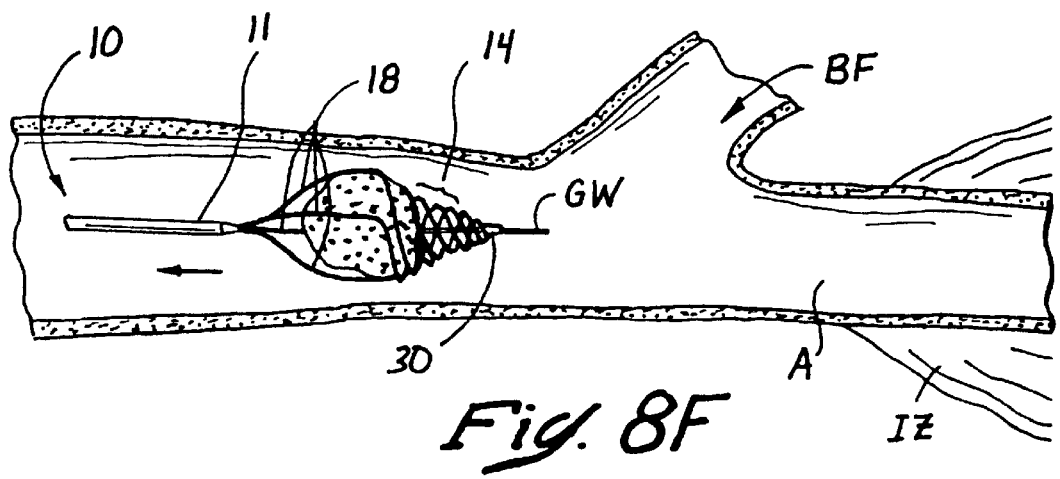
Figure 9A:
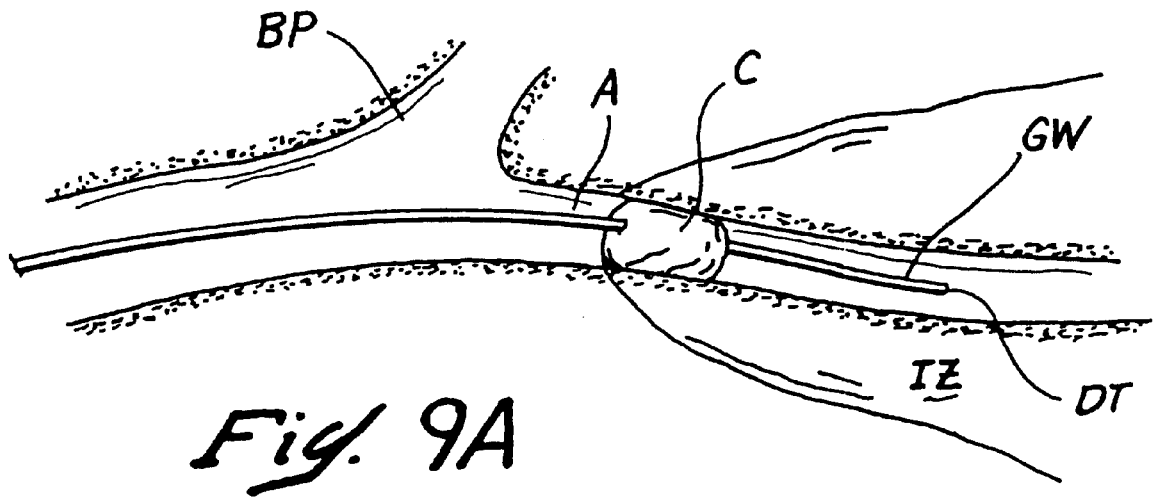
FIGS. 9a–9d are step-wise showings of a procedure wherein the third embodiment (i.e., a rapid exchange embodiment) of an embolectomy catheter of the present invention is used to remove a blood clot from a small blood vessel of a mammalian body.
Figure 9B:
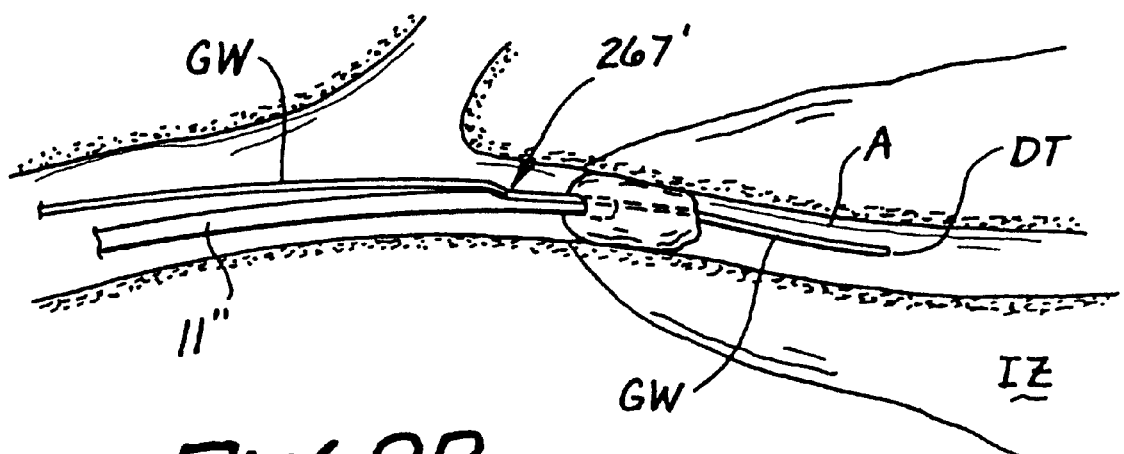
Figure 9C:
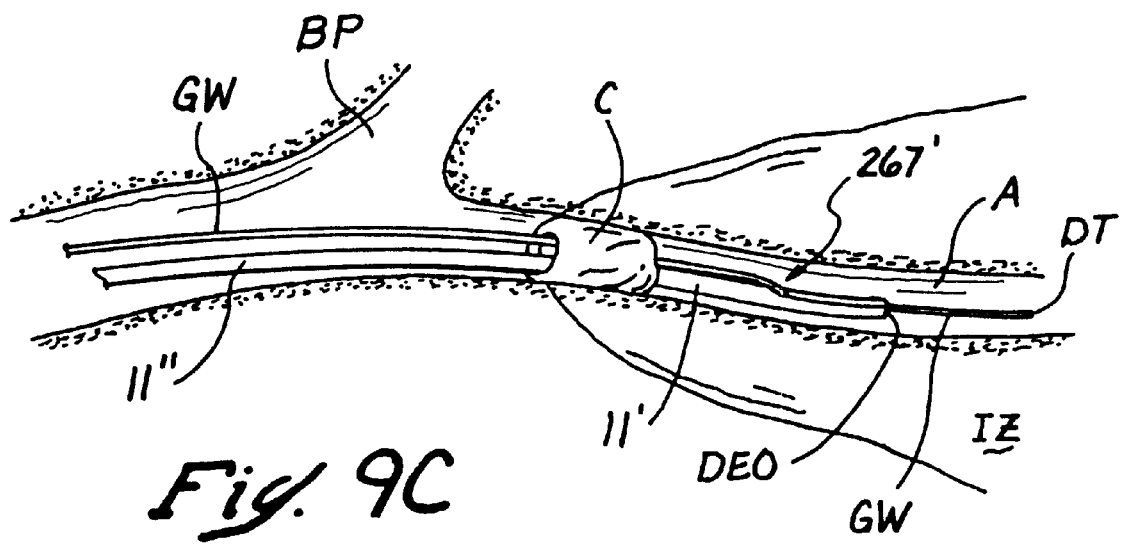

Methods for Using the Invention to Remove Clots or Other Obstructive Matter from Blood Vessels FIGS. 8a–8f illustrate a preferred method of using an the over-the-wire type embolectomy catheter 10 of the invention to remove a obstructive matter such as a thromboembolism or blood clot, while FIGS. 9a–9c illustrate a preferred method of using a rapid exchange type embolectomy catheter 10" of the invention to remove such obstructive matter. These exemplary procedures are described in detail in the paragraphs below.

Preferred Use of the Over-the-Wire Embolectomy Catheter

FIGS. 8a–8f show a presently preferred method for using the over-the-wire type embolectomy catheter 10 shown in FIGS. 1–2d to remove a thromboembolus or clot C which has become lodged immediately downstream of an arterial bifurcation BE so as to create an ischemic zone IZ of tissue (e.g., brain tissue which is deprived of oxygen and other nutrients) located downstream of the clot C. The preferred procedures depicted in these drawings are described in the paragraphs herebelow.

Initially, a microcatheter such as the rapid exchange microcatheter 265 of FIG. 3c (not shown in FIGS. 8a–8f) is advanced to a position near the obstructive matter or clot C and radiographic contrast medium is injected through the microcatheter to angiographically verify the precise location of the clot C and to visualize or map the anatomy of the blood vessels in the area of the clot. Thereafter, a guidewire having a diameter of 0.01–0.014 inches and a length which is not more than 1.5 times the length of the microcatheter 265 (i.e., not an "exchange-length" guidewire) is advanced from the lumen 271 of the microcatheetr 265 until its distal tip DT has passed through the clot C as shown in FIG. 8a.

Threrafter, the operator will hold the proximal end of the guidewire GW to prevent longitudinal retraction of the guidewire GW while retracting and removing the rapid exchange microcatheter 265. This allows the guidewire GW to remain in its operative position as shown in FIG. 8a.

Thereafter, as shown in FIG. 8b, the embolectomy catheter 11 having its obstructive matter capturing receptacle retracted to its first configuration (FIG. 2a) is advanced over the guidewire GW and through the clot C, such that the distal end opening DEO of the catheter 11 is located downstream of the clot C but still proximal to (i.e., upstream of) the distal tip DT of the guidewire GW.

Thereafter, as shown in FIGS. 8c and 8d, the actuator 28 is advanced in the distal direction to cause the four wire segments 20 which form the obstructive matter capturing receptacle 14 to advance out of the distal end of the catheter such that the nose cone 30 remains upon the guidewire GW. In this manner, the obstructive matter capturing receptacle 14 is fully deployed to its second or operative configuration at a location distal to (i.e., downstream of) the clot C (FIG. 3d).

Thereafter, as shown in FIG. 8e, the embolectomy catheter 11 is retracted in the proximal direction to cause the proximal connector members 18 of the obstructive matter capturing receptacle 14 to pass through the clot, and to further cause the clot to be received within the concave or cavernous interior of the distal obstructive matter receiving portion 16 of the receptacle 14, as shown.

Thereafter, as shown in FIG. 8f, the entire embolectomy catheter device 10, with the clot C in tow, may be retracted out of the body—or to a location within a larger blood vessel (e.g., carotid artery) where the clot C and the fully deployed obstructive matter capturing receptacle 14 may be received within the lumen of a larger catheter to further secure the clot for ultimate extraction and removal form the body.

Preferred Use of the Rapid Exchange Embolectomy Catheter

The preferred method of using a rapid exchange type embolectomy catheter of this invention 10" is shown in FIGS. 9a–9d.

Initially, a microcatheter such as the rapid exchange microcatheter 265 of FIG. 3c (not shown in FIGS. 9a–9d) is advanced to a position near the clot C and radiographic contrast medium is injected through the microcatheter to angiographically verify the precise location of the clot C and to visualize or map the anatomy of the blood vessels in the area of the clot. Thereafter, a guidewire having

E. Methods for Using the Invention to Remove Clots or Other Obstructive Matter from Blood Vessels FIGS. 8a–8f illustrate a preferred method of using an the over-the-wire type embolectomy catheter 10 of the invention to remove a obstructive matter such as a thromboembolism or blood clot, while FIGS. 9a–9c illustrate a preferred method of using a rapid exchange type embolectomy catheter 10" of the invention to remove such obstructive matter. These exemplary procedures are described in detail in the paragraphs below.

Preferred Use of the Over-the-Wire Embolectomy Catheter

FIGS. 8a–8f show a presently preferred method for using the over-the-wire type embolectomy catheter 10 shown in FIGS. 1–2d to remove a thromboembolus or clot C which has become lodged immediately downstream of an arterial bifurcation BE so as to create an ischemic zone IZ of tissue (e.g., brain tissue which is deprived of oxygen and other nutrients) located downstream of the clot C. The preferred procedures depicted in these drawings are described in the paragraphs herebelow.

Initially, a microcatheter such as the rapid exchange microcatheter 265 of FIG. 3c (not shown in FIGS. 8a–8f) is advanced to a position near the obstructive matter or clot C and radiographic contrast medium is injected through the microcatheter to angiographically verify the precise location of the clot C and to visualize or map the anatomy of the blood vessels in the area of the clot. Thereafter, a guidewire having a diameter of 0.01–0.014 inches and a length which is not more than 1.5 times the length of the microcatheter 265 (i.e., not an "exchange-length" guidewire) is advanced from the lumen 271 of the microcatheetr 265 until its distal tip DT has passed through the clot C as shown in FIG. 8a.

Threrafter, the operator will hold the proximal end of the guidewire GW to prevent longitudinal retraction of the guidewire GW while retracting and removing the rapid exchange microcatheter 265. This allows the guidewire GW to remain in its operative position as shown in FIG. 8a. a *diameter of* 0.006–0.018 inches and a length which is not more than 1.5 times the length of the microcatheter 265 (i.e., not an "exchange-length" guidewire) is advanced from the lumen 271 of the microcatheetr 265 until its distal tip DT has passed through the clot C as shown in FIG. 9a.

Threrafter, the operator will hold the proximal end of the guidewire GW to prevent longitudinal retraction of the guidewire GW while retracting and removing the rapid exchange microcatheter 265. This allows the guidewire GW to remain in its operative position as shown in FIG. 9a.

Thereafter, as shown in FIG. 9b, the exteriorized proximal end of the guidewire is inserted into the distal end opening DEO of the the rapid exchange embolectomy catheter 11" while its obstructive matter capturing receptacle is retracted to its first configuration (FIG. 2a) within the distal portion of the catheter 11'. As the catheter is advanced in the distal direction over the guidewire GW, the guidewire will be deflected by the guidewire deflection tube 260' (see FIG. 3d) and the proximal end of the guidewire will emerge out of the side guidewire passage aperture 267' of the catheter 11". The catheter 11" is advanced through the clot C, such that the distal end opening DEO of the catheter 11" is located downstream of the clot C but still proximal to (i.e., upstream of) the distal tip DT of the guidewire GW, as shown in FIG. 9c. The guidewire GW extends along side of the proximal portion of the rapid exchange catheter 11" (i.e., the portion of the catheter proximal to the guidewire passage aperture 267'), as shown.

Figure 9D:
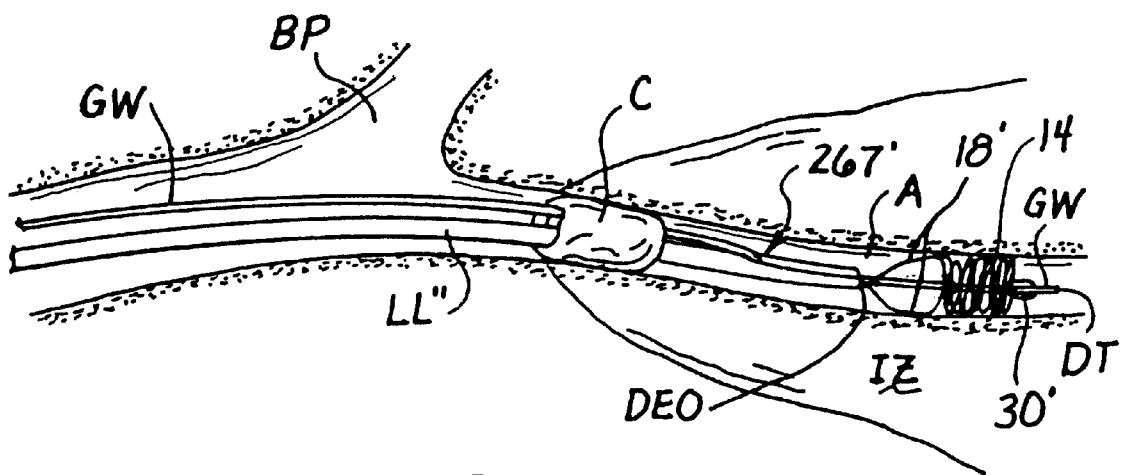

Thereafter, as shown in FIG. 9d, the actuator 28 is advanced in the distal direction to cause the two (2) wire members 20' which form the obstructive matter capturing receptacle 14' to advance out of the distal end of the catheter 11' such that the nose cone 30' remains upon the guidewire GW. In this manner, the obstructive matter capturing receptacle 14' is fully deployed to its second or operative configuration at a location distal to (i.e., downstream of) the clot C (FIG. 9d).

Thereafter, the rapid exchange embolectomy catheter 11' is retracted in the proximal direction to cause the proximal connector members 18' of the obstructive matter capturing receptacle 14' to pass through the clot, and to further cause the clot to be received within the concave or cavernous interior of the helical basket 16' of the receptacle 14'. The clot C is then removed by retraction of the catheter 11', in the same manner shown and described above and shown in FIGS. 8e and 8f.

It is to be appreciated that the invention has been described herein with reference to certain exemplary embodiments only, and no effort has been made to exhaustively describe each an every possible embodiment of the invention. Indeed, as those skilled in the art will appreciate, various additions, deletions, modifications and/or alterations may be made to he above described embodiments without departing from the spirit and scope of the invention. It is intended that all such additions, deletions, alterations and modifications be included within the scope of the following claims.

What is claimed is:

1. An embolectomy catheter device for removing a blood clot or other obstructive matter from a blood vessel, said device comprising:

an elongate flexible catheter body having a proximal end, a distal end, and a guidewire lumen which extends longitudinally through at least a portion thereof, wherein a plurality of member guide passageways extend through the distal end of the catheter; and an obstructive matter capturing receptacle which is initially disposed in a first stowed configuration which is passable through the obstructive matter, and is subsequently deployable to a second radially expanded configuration, the obstructive matter capturing receptacle comprises a plurality of elongate members which are preformed to generally helical configurations, and which extend through the guide passageways formed in the distal end of the catheter, said elongate members being retractable in a proximal direction through said guide passageways whereby they will assume substantially straight configurations;

said obstructive matter capturing receptacle having a guidewire passageway which extends longitudinally therethrough in alignment with the guidewire lumen of said catheter body, such that the obstructive matter capturing receptacle and the catheter body may be advanced over a previously positioned guidewire, said elongate members being advanceable in a distal direction through said guide passageways such that they will assume their generally helical configurations and will form said clot capturing receptacle.

2. The embolectomy catheter device of claim 1 wherein the obstructive matter capturing receptacle is sufficiently porous to allow blood to flow therethrough, but sufficiently non-porous to prevent a blood clot from passing therethrough.

3. The embolectomy catheter device of claim 2 wherein said obstructive matter capturing receptacle has openings of 100–1000 microns formed therein, to provide a porosity of 25% to 90%.

4. The embolectomy catheter device of claim 1 wherein the obstructive matter capturing receptacle is formed of pre-formed, elastic material which collapses to said first configuration when retracted into the catheter, and expands to said second configuration when advanced out of said catheter.

5. The embolectomy catheter of claim 4 wherein the obstructive matter capturing receptacle is formed of a material which is superelastic at body temperature.

6. The embolectomy catheter of claim 5 wherein the obstructive matter capturing receptacle is formed of a nickel-titanium alloy which is superelastic at body temperature.

7. The embolectomy catheter device of claim 1 further comprising:

a proximal connector formed on the proximal end of the catheter body, said proximal connector having an injection port formed therein to permit radiographic contrast medium to be injected through a lumen of the catheter body while a guidewire is positioned within the guidewire lumen of the catheter body.

8. The embolectomy catheter device of claim 1 wherein distal portions of said elongate members will, when unconstrained, form a distal obstructive matter receiving portion of the receptacle and proximal portions of said elongate members will form struts which extend from the catheter body to the distal obstructive matter receiving portion of the receptacle.

9. The embolectomy catheter device of claim 8 wherein said struts are configured and positioned to pass through a clot when withdrawn therethrough in a proximal direction, but the distal obstructive matter receiving portion of the receptacle is sufficiently dense to prevent that clot from passing therethrough.

10. An over the wire embodiment of the embolectomy catheter of claim 1 wherein the guidewire lumen extends longitudinally through substantially the entire catheter body.

11. The embolectomy catheter device of claim 1 wherein the catheter body is of greater flexibility near its distal end than near its proximal end.

12. The embolectomy catheter device of claim 11 wherein at least a portion of the catheter body between its proximal and distal ends is of gradually increasing flexibility over its entire length.

13. The embolectomy catheter device of claim 11 wherein the catheter body comprises at least two discrete regions of differing flexibility.

14. The embolectomy catheter device of claim 11 wherein the catheter body comprises at least two discrete regions of differing diameter.

15. The embolectomy catheter device of claim 14 wherein said discrete regions of differing diameter are also of differing flexibility.

16. The embolectomy catheter of claim 1 wherein the obstructive matter capturing receptacle and catheter body are constructed so as to be extractable, with the removed obstructive matter, through a percutaneous vascular access tract.

17. A rapid exchange embodiment of the embolectomy catheter of claim 1 wherein the catheter device further comprises a guidewire passage aperture formed in the catheter body a spaced distance proximal to the distal end thereof, and wherein the guidewire lumen of the catheter body extends at least from the guidewire passage aperture to the distal end of the catheter body.

18. The embolectomy catheter device of claim 17 further comprising a guidewire deflector positioned within the guidewire lumen of the catheter body and configured to deflect the proximal end of a guidewire out of the guidewire passage aperture, as the catheter body is advanced in the distal direction over the guidewire.

19. The embolectomy catheter device of claim 18 wherein the guidewire deflector comprises a curved guidewire deflector tube having a proximal end positioned at the guidewire passage aperture and a distal end positioned within the guidewire lumen of the catheter such that the proximal end of the guidewire will be received within the distal end of the curved guidewire deflector tube and will thereafter pass through the curved guidewire deflector tube and out of the guidewire passage aperture.

20. The embolectomy catheter device of claim 19 wherein the distal end of the curved guidewire deflector tube is larger in diameter than the rest of the curved guidewire deflector tube to facilitate entry of the proximal end of the guidewire into the distal end of the curved guidewire deflector tube.

21. The embolectomy catheter device of claim 19 wherein at least one support member is attached to the distal end of the curved guidewire deflector tube to hold the distal end of the curved guidewire deflector tube in a substantially centered position within the guidewire lumen of the catheter.

22. The embolectomy catheter device of claim 19 wherein the guidewire lumen of the catheter body additionally extends through the portion of the catheter body proximal to the guidewire passage aperture and is used for injection of radiographic contrast medium as well as for passage of the guidewire and wherein at least one flow passageway is formed adjacent the distal end of the curved guidewire deflector tube to allow radiographic contrast medium to flow past the curved guidewire deflector tube and out of the distal end of the catheter body.

23. The embolectomy catheter device of claim 1 further comprising a tip member formed on the distal ends of said elongate members, said guidewire lumen of the receptacle extends through said tip member.

\* \* \* \* \*